(12) United States Patent
Rhodes, Jr. et al.

(10) Patent No.: US 10,079,966 B2
(45) Date of Patent: Sep. 18, 2018

(54) SYSTEMS AND TECHNIQUES FOR CAPTURING IMAGES FOR USE IN DETERMINING REFLECTANCE PROPERTIES OF PHYSICAL OBJECTS

(71) Applicant: ADOBE SYSTEMS INCORPORATED, San Jose, CA (US)

(72) Inventors: Tenell Rhodes, Jr., Philadelphia, PA (US); Gavin Miller, Los Altos, CA (US)

(73) Assignee: ADOBE SYSTEMS INCORPORATED, San Jose, CA (US)

( * ) Notice: Subject to any disclaimer, the term of this patent is extended or adjusted under 35 U.S.C. 154(b) by 76 days.

(21) Appl. No.: 15/374,990

(22) Filed: Dec. 9, 2016

(65) Prior Publication Data

US 2018/0165820 A1 Jun. 14, 2018

(51) Int. Cl.
  *H04N 5/225* (2006.01)
  *G06T 7/507* (2017.01)
(52) U.S. Cl.
  CPC ........... *H04N 5/2256* (2013.01); *G06T 7/507* (2017.01)
(58) Field of Classification Search
  None
  See application file for complete search history.

(56) References Cited

U.S. PATENT DOCUMENTS

2014/0126835 A1\* 5/2014 Shioya .................... G06T 5/008
  382/274
2015/0285903 A1\* 10/2015 Bridges ................ G01C 15/002
  356/4.01

OTHER PUBLICATIONS

Yu et al., "Inverse Global Illumination: Recovering Reflectance Models of Real Scenes from Photographs", SIGGRAPH '99 Proceedings of the 26th annual conference on Computer graphics and interactive techniques pp. 215-224, ACM Press/Addison-Wesley Publishing Co. New York, NY, USA © 1999.
Abrams, Bryan. "USC's Paul Debevec's Role in The Matrix, Avatar, Gravity & More", Wheretowatch.com, Oct. 29, 2013. Web. (17 pages) https://www.wheretowatch.com/2013/10/uscs-paul-debevec-s-role-in-the-matrix-avatar-gravity-more.

\* cited by examiner

*Primary Examiner* — Mark T Monk
(74) *Attorney, Agent, or Firm* — Brake Hughes Bellerman LLP

(57) ABSTRACT

Systems and techniques are disclosed that use an image capture device to capture images of an object under specified image capture conditions for use in determining reflectance properties of the object. Images of the object are captured from a variety of different camera directions and with the object illuminated from a variety of different light directions. To capture these images, a camera of the image capture device is moved relative to the object and lights of the device are selectively illuminated. The image capture device has various features that increase the variety and number of different image capture conditions that can be captured. For example, using planar arrays of individually addressable lights in the image capture device allows tens, hundreds, or even thousands of lights to be used. Using planar arrays of lights provides light from many different directions without adding substantial complexity or cost to the device.

20 Claims, 10 Drawing Sheets

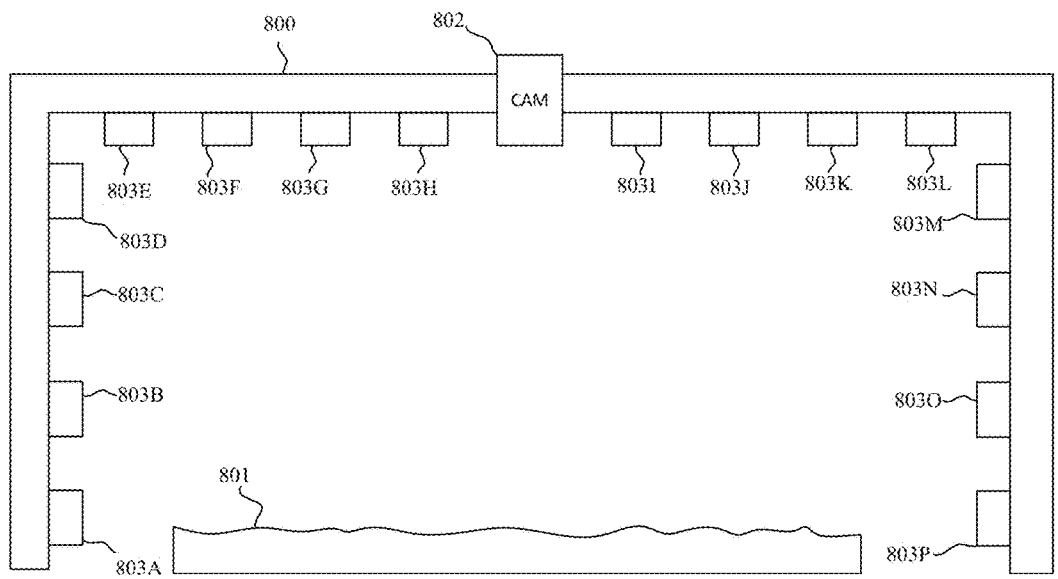
FIGURE 8
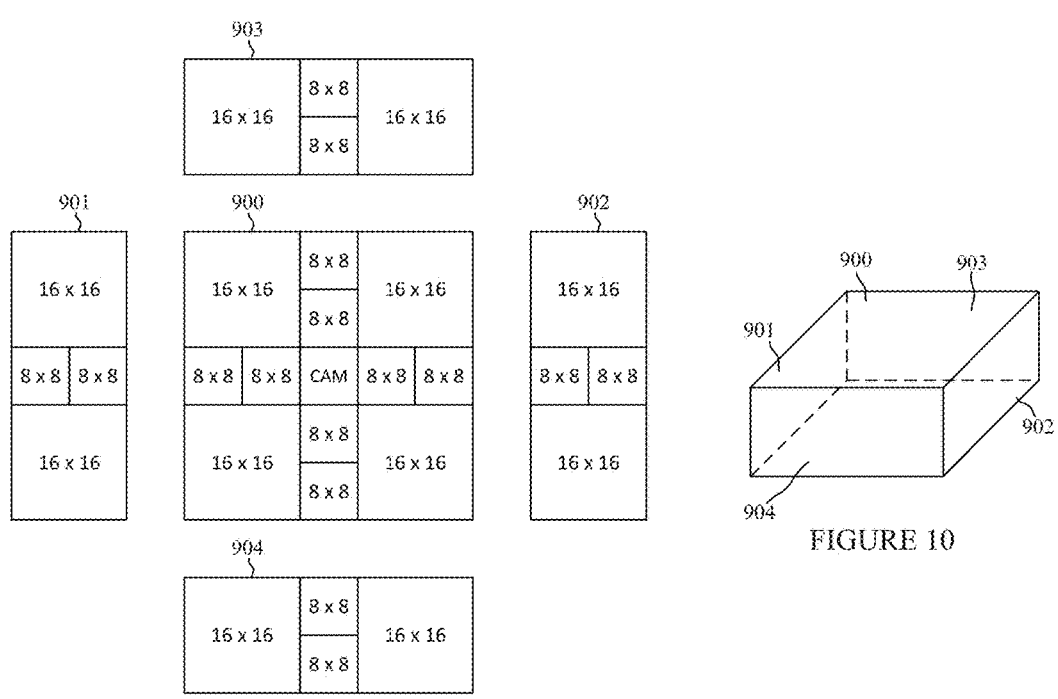
FIGURE 9
FIGURE 10

SYSTEMS AND TECHNIQUES FOR CAPTURING IMAGES FOR USE IN DETERMINING REFLECTANCE PROPERTIES OF PHYSICAL OBJECTS

TECHNICAL FIELD

This disclosure relates generally to systems and techniques used to capture images for use in determining reflectance properties of physical objects and more particularly relates to capturing images of objects under variable image capture conditions to determine reflectance properties of such objects.

BACKGROUND

Various techniques are used to determine reflectance properties of physical objects. Such reflectance properties can be used to provide photorealistic 2 dimensional (2D) and 3 dimensional (3D) renderings of the objects and for a variety of other purposes. For example, the reflectance properties of an object can specify the color of a portion of an object for different lighting conditions in which light strikes the surfaces of the object from different directions and for various viewing angles. Existing techniques used to determine reflectance properties of physical objects generally involve taking pictures of an object from different, known camera and light directions and using the information in the captured images to compute the reflectance properties of the object. These captured reflectance properties can be modeled as a bi-directional reflectance distribution function (BRDF). A BRDF provides a way to lookup or otherwise determine what the color of each pixel of a 2D or 3D representation of the object is for given light and camera directions.

Existing devices used to capture images of physical objects to determine reflectance properties of the objects have several limitations and are especially ill-suited for capturing the reflectance properties of objects that include spatially-varying materials. A spatially-varying material is a material that changes appearance depending on the viewer's viewing direction and the direction that light strikes the material. For example, the apparent color of gold leaf material changes depending on the angle from which the viewer looks at it and from where the light is coming. Looking at a surface of gold leaf, the surface will appear to have different colors in different places on the surface due to this characteristic. Some existing devices used to capture images of an object to determine reflectance properties use a dome structure with approximately 20 lights in different positions on the inside of the dome along with a camera to capture images of the object given light from each of the lights. The limited number of lights and limited range of movement of these devices significantly reduces the resolution and accuracy of the reflectance properties that the devices can capture. The number of lights is limited based on the significant expense of positioning lights on a dome structure as well as the complexity of controlling the lights individually in such a structure. Generally, existing devices and techniques do not provide a sufficiently precise and cost effective way to capture reflectance properties of physical objects, especially those that include spatially-varying materials with rapidly changing angular dependence on view angle or lighting.

SUMMARY

Systems and techniques are disclosed that use an image capture device to capture images of an object under specified image capture conditions for use in determining reflectance properties of the object. Images of the object are captured from a variety of different camera directions and with the object illuminated from a variety of different light directions. To capture these images, a camera of the image capture device is moved relative to the object and lights of the device are selectively illuminated. The image capture device has various features that increase the variety and number of different image capture conditions that can be captured. For example, using planar arrays of individually addressable lights in the image capture device allows tens, hundreds, or even thousands of lights to be used. Using planar arrays of lights provides light from many different directions without adding substantial complexity or cost to the device. Capturing images of an object under a larger variety of image capture conditions allows reflectance properties of the object to be determined with better accuracy and higher resolution.

One embodiment of the invention is a system for capturing images used to determine reflectance properties of an object. The system includes an image capture device that captures images of the object based on instructions received from a computing device. The image capture device includes a light assembly, a camera, and a motor. The light assembly has a planar array of lights attached to a surface of the light assembly. The lights are individually addressable and configured to illuminate based on receiving lighting instructions. The camera is attached to the light assembly in a position relative to the lights to receive light from an object illuminated by the lights to capture images of the object. The camera is also configured to capture images of the object based on receiving camera instructions. The motor is attached to the light assembly and configured to move the lights and camera relative to the object based on receiving motor instructions. The computing device performs operations to control the image capture device. The computing device identifies image capture conditions for capturing images for use in determining reflectance properties of the object. The image capture conditions specify capturing the images of the object from multiple camera directions and with the object illuminated from multiple lighting directions. The computing device uses the identified image capture conditions to provide instructions to the image capture device to position the camera using the motor, selectively illuminate one or more of the lights, and capture the images of the object under the variety of image capture conditions.

Another exemplary embodiment of the invention is a method for capturing images used to determine reflectance properties of an object. The method identifies image capture conditions for capturing images for use in determining reflectance properties of the object. The method determines camera and light configurations for an image capture device to capture the images under the image capture conditions. The method controls the image capture device to capture the images using the camera and light configurations. This involves controlling the planar array of lights, the camera, and the motor of the image capture device. Specifically, the method provides instructions to the image capture device to position the planar array of lights and camera using the motor, illuminate one or more of the lights of the planar array of lights, and capture the images under the image capture conditions using the camera.

These illustrative features are mentioned not to limit or define the disclosure, but to provide examples to aid understanding thereof. Additional embodiments are discussed in the Detailed Description, and further description is provided there.

BRIEF DESCRIPTION OF THE FIGURES

These and other features, embodiments, and advantages of the present disclosure are better understood when the following Detailed Description is read with reference to the accompanying drawings.

FIG. 8 is a cross sectional view of an exemplary image capture apparatus with a partial-cube shaped light assembly.

FIG. 9 illustrates multiple connected planar arrays of lights configured to be combined as the sides of an exemplary light assembly.

FIG. 10 is an isometric view of the exemplary light assembly of FIG. 9 with the sides connected to one another in a partial-cube-shaped light assembly.

DETAILED DESCRIPTION

Figure 1:
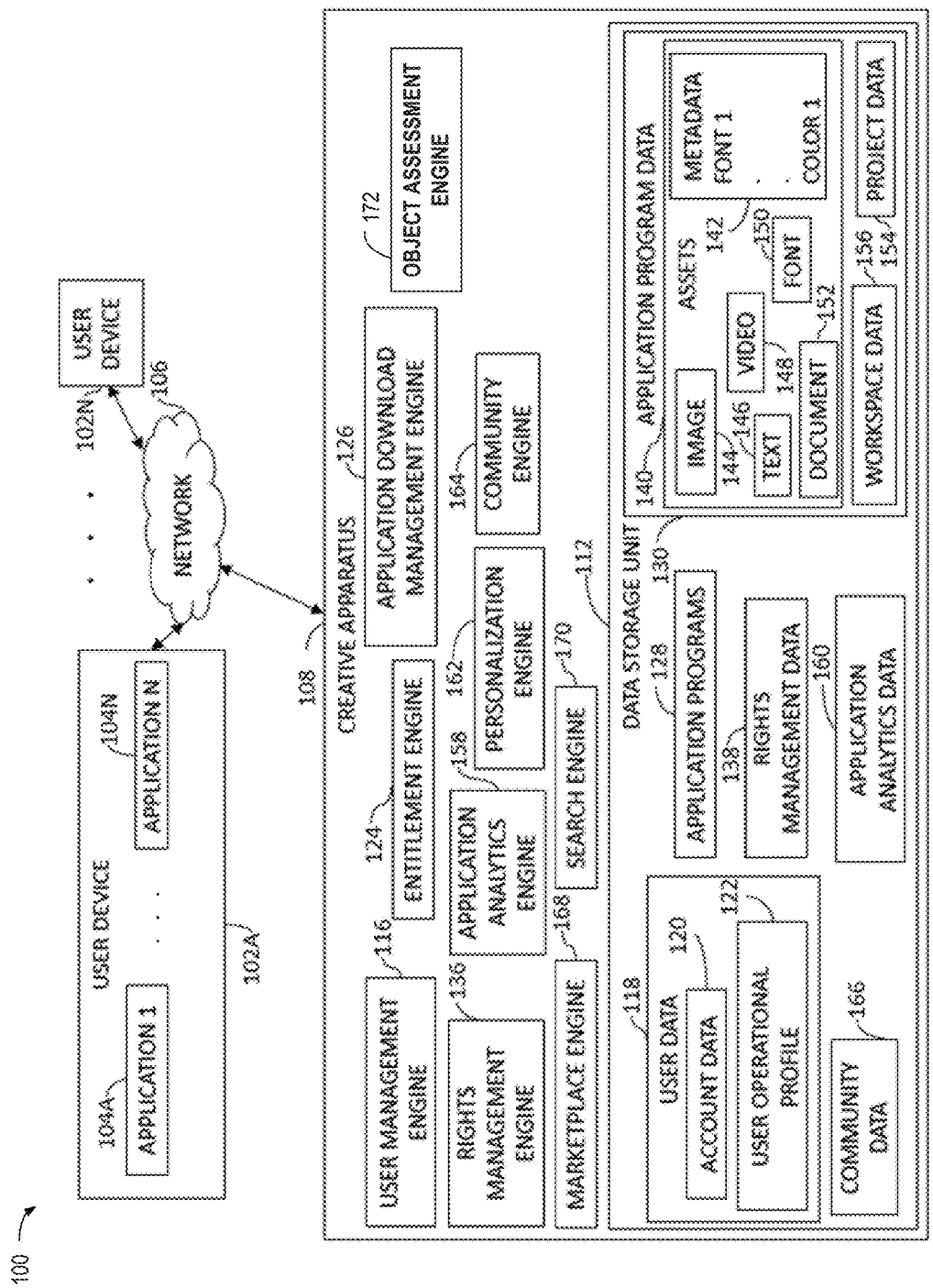
FIG. 1 is a diagram of an environment in which one or more techniques of the invention can be practiced.

As discussed above, existing systems and techniques do not provide a sufficiently precise and cost effective way to capture reflectance properties of physical objects, especially objects that include spatially-varying materials with high angular variation of appearance. Embodiments of the invention provide more cost effective and more precise ways of capturing reflectance properties of physical objects. The systems and techniques disclosed herein control an image capture device to capture images of an object under a larger variety of image capture conditions than prior systems and techniques. Various features of the image capture device are configured to increase the variety and number of different image capture conditions that can be captured and/or to reduce the complexity and cost of the device. Examples of these features of image capture devices include, but are not limited to, planar arrays of individually addressable lights, motors to move cameras and/or lights, wide angle camera lenses, and legs that are shaped to enable a greater range of movement of the cameras and/or lights. Using one or more of these features, an image capture device is able to capture images of an object under a greater number of image capture conditions and with more variety than prior systems and techniques. Capturing images of the object from a greater number and variety of image capture conditions allows reflectance properties of the object to be determined with better accuracy and higher resolution.

Systems and techniques disclosed herein control an image capture device to capture images under a variety of image capture conditions. In one example, a camera and light assembly of the image capture device is moved to various locations above the object to capture images of the object from the camera directions associated with each of those camera positions. In this example, the camera and light assembly are moved to a first position above the object at which the camera is positioned to capture images from a particular camera direction. Multiple images of the object are captured with the camera in this position. For these different images, different lights are illuminated to illuminate the object from different light directions. For example, the device can have thousands of LEDs that are individually illuminated to capture thousands of images of the object with the camera in the first position. The camera and light assembly are then moved to a second position above the object at which the camera is positioned to capture images from a different camera angle. Multiple images of the object are then captured with the camera in this second position with different lights illuminated. This process continues to for many additional camera positions to compile a large set of images of the object captured under a large variety of different image capture conditions.

The greater the number of images captured under varying image capture conditions, the greater accuracy and resolution of the reflectance properties that can be determined using the images. Accordingly, the image capture conditions can be selected to achieve a desired accuracy level. For example, only a small number of image capture conditions can be specified for certain types of objects while a larger number of image capture conditions can be specified for other types of objects. This flexibility allows the image capture device to be used for a variety of materials, circumstances, and user preferences.

Embodiments of the invention use one or more features on an image capture device to provide better accuracy, cost effectiveness, and performance than prior systems and techniques. For example, embodiments of the invention provide image capture devices that use a light assembly with a planar array of lights or a partial cube shape with many individually addressable lights. Using such planar arrays or partial cube light assemblies allows the devices to provide a higher density of lights without significantly adding to the complexity or cost of the device. In addition, inexpensive, off-the-shelf components providing flat, dense arrays of LED (or other lights) can be combined to form the planar array or partial cube light assembly. The use of such off-the-shelf can further reduces the cost and complexity of the device. For example, in comparison, the dome-shaped light assemblies of certain prior devices could not use these flat-surfaced components and instead required that the lights be attached to the dome and wired individually at a significantly greater expense.

Embodiments of the invention provide techniques that eliminate the constraint of using dome-shaped light assemblies. Dome-shaped light assemblies were used to provide individual lights at approximately the same distance from the object because the calculations used to determine the reflectance properties of the object required those equidistance relationships. Techniques of embodiments of the invention eliminate the need to use lights at approximately the same distance from the object and thus eliminate the need to use a dome-shaped light assembly. These techniques determine the reflectance properties of an object using adjustments to the captured images of the object that account for differences in the individual lights. These adjustments account for the fact that one light may be farther away from the object than another light, as well as other differences that the lights may have relative to one another. These adjustments are made based on a calibration process that assesses light differences using one or more sample objects. By being able to adjust for differences between lights, these techniques enable use of a non-dome shaped light assembly. The non-dome shaped light assembly in turn can be planar and thus include many more lights to determine the reflectance properties of objects at higher resolution and lower cost that prior devices and techniques. In one example, the light assembly includes over 4,000 LED lights that can be used to create a high resolution light array for BRDF determinations. Such a structure that includes hundreds or thousands of lights is particularly useful for BRDF determinations for objects that include materials that are highly view dependent, such as materials that are spatially-varying, highly specular, self-occluding, sparkly, etc.

Embodiments of the invention additionally or alternatively use one or more motors to move the camera and/or light assembly relative to the object. Using off the shelf motors to move the camera and/or light assembly can reduce the complexity and cost of the image capture device. In one example, the image capture device uses a relatively inexpensive, off-the-shelf x, y, z, gantry with three motors that can move the camera and/or light assembly along three axis of movement to enable a large number of image capture conditions.

Embodiments of the invention additionally or alternatively attached the camera to the light assembly so that the camera and light assembly are moved together. Attaching the camera to the light assemblies allows the camera to be moved without blocking the lights or being blocked by the lights. The camera and light assembly are flexible to be moved together to capture images of the object under the variable image capture conditions. Being able to move the camera and light assembly without being constrained by the possibility of one blocking the other can further increase the image capture conditions that the image capture device can use.

Embodiments of the invention additionally or alternatively provide devices that use a wide angle lens to provide various benefits. Using a wide angle lens allows the camera of the device to capture images of the object from a greater variety of angles and positions. For example, in addition to capturing images of the object while the camera is positioned directly above the object, the camera can be moved laterally above the object and capture images of the object from additional viewing directions. The wide angle lens ensures that the images from the camera are able to capture the object even when the camera is not positioned directly above the object. It also avoids the need to change the orientation of the camera itself. The optical resolution of the wide angle lens may be less than that of narrow angle lenses. However, this difference in optical resolution is offset when the wide angle lens is used with a light assembly with a relatively larger number of lights and at relatively short range (e.g., 9 inches) from the object. The images captured from such a device allow determining higher resolution reflectance properties of an object even though the optical resolution of the lens itself may be less. While a narrow angle lens can be used in certain circumstances, a wide angle lens is advantageous in many circumstances. For example, a narrow angle lens could be rotated to take several images to cover the same solid angle of capture as a single image from wide angle lens. However, using a wide-angle lens can allow for more rapid capture of the scene. The more rapid capture time of a wide angle lens implementation is especially advantageous in circumstances involving a large number of captured images. In such circumstances, the additional time to reorient the narrow angle lens and the number of additional image captures required can be significant disadvantages.

Embodiments of the invention additionally or alternatively provide a frame that provides advantages. In one embodiment, the legs of the frame of the device are configured to provide support and stability for the light assembly and/or camera. The legs are also configured to project outward, away from the object. The outwardly projecting legs provide a greater degree of freedom to move the lights and/or camera. For example, the lights and/or camera can be moved farther to the side without being obstructed by a leg of the support structure. This additional lateral mobility increases the image capture conditions under which images of an object can be captured. The frame can additionally, or alternatively, be configured to allow the lights and/or camera to be moved up and down in the z direction in addition laterally in the x, y directions. The additional vertical mobility is particularly useful for example in assessing objects that have significant depth variations such as sculptures, toys, animals, people, and other real objects that have depth variations.

The embodiments of the invention disclosed herein provide systems and techniques that provide numerous benefits over prior devices and techniques. The systems and techniques provide less expensive devices that can provide images for capturing higher resolution reflectance properties of objects. Moreover, the systems and techniques enable capturing reflectance properties for a variety of materials including, but not limited to, oil paintings, spatially-varying materials, naturally occurring surfaces, and antique photographic prints, etc.

Terminology

As used herein, the phrase "computing device" refers to any electronic component, machine, equipment, or system that can be instructed to carry out operations. Computing devices will typically, but not necessarily, include a processor that is communicatively coupled to a memory and that executes computer-executable program code and/or accesses information stored in memory or other storage. Examples of computing devices include, but are not limited to, desktop computers, laptop computers, server computers, tablets, telephones, mobile telephones, televisions, portable data assistant (PDA), e-readers, portable game units, smart watches, etc.

As used herein, the phrase "image" refers to a photograph or other representation of an object captured by a camera. For example, an image of an object can include a set of data representing color values of pixels that provide a visual representation of the object from a particular viewing direction. "Capturing" an image of an object refers to creating a representation of the object using an electronic sensor or photographic film. An image can be an individual, still image or can be a sequence of images constituting a video.

As used herein, the phrase "reflectance property" refers to the variance of color of a portion of an object for different lighting conditions. For example, the color of the portion of an object can depend on the lighting and/or viewing direction. The color of the portion of the object includes the hue, value, intensity, or any other appropriate appearance attribute of the portion of the object. Reflectance properties of an object can be modeled as a bi-directional reflectance distribution function (BRDF). A BRDF provides a way to lookup or otherwise determine what the color of each pixel of a 2D or 3D representation of the object is for given light and camera directions.

As used herein, the phrase "object" refers to any tangible real world thing. Objects include papers, paintings, films, and other flat surfaces as well as sculptures, rocks, minerals, plants, metals, plastics, and other things having depth. Generally, anything that can be photographed from multiple camera positions and/or lighting conditions can be considered an object herein.

As used herein, the phrase "camera" refers to a device capable of recording images of an object using an electronic sensor or photographic film. For example, one example of a camera is an optical instrument for capturing images that are stored locally on the camera, transmitted to another device, or both. A camera generally captures a representation of an object by capturing light received from the object without physical contact with the object.

As used herein, the phrase "lighting condition" refers to an attribute of the light that illuminates an object while an image of the object is captured. Lighting conditions during the capturing of images of an object using a camera can depend upon the direction of the light relative to the object, the distance of the light from the object, the orientation of the light and/or object, and the color of the light, among other things.

As used herein, the phrase "image capture condition" refers to a particular camera direction relative to an object and a particular light direction of a light illuminating the object as the object is captured by the camera. Image capture conditions can be varied, for example, by varying a camera position relative to the object, a light assembly position relative to the object, and/or by selecting which lights of the light assembly illuminate the object during the image capture.

As used herein, the phrase "planar surface" refers to a flat surface. Dome-shaped surfaces are not planar surfaces.

As used herein, the phrase "light" refers to something that produces light rays to illuminate an object. Lights include, but are not limited to, incandescent light bulbs, compact fluorescent light bulbs, fluorescent light bulbs, light emitting diodes (LEDs).

As used herein, the phrase "motor" refers to a component that converts electrical energy into mechanical motion. For example, a motor can be used to move an image capture apparatus along one or more axes of motion.

As used herein, the phrase "frame" refers to a structure that resists load to provide support through interconnected structural components or members. For example, a frame can include one or more supports, such as legs, that extend to a floor, wall, or other external feature to provide support. The structural system of components or members of a frame transfers load through the interconnected components or members of the structural system.

As used herein, the phrase "support" refers to a component or member of a frame that resists or transfers load. Examples of supports include legs, braces, and rods that resist or transfer load in a frame.

As used herein, the phrase "external feature" refers to a floor, wall, platform, stand, or other thing that a support interacts with to resist load. For example, legs of a frame can extend down to an underlying floor surface to support an image capture apparatus above an object.

As used herein, the phrase "planar array" refers to a planar, i.e., flat, surface upon which a number of items are positions. For example, a planar array of lights includes a number of lights positioned on a flat surface. The lights in this example can be spaced at regular intervals on the surface.

As used herein, the phrase "serially-connected" refers to lights that are connected to one another in a series. Control information can be passed from one light to the next in a set of serially-connected lights to individually control the lights.

As used herein, the phrase "partial cube" refers to part of the surfaces of a cube. For example, a shape comprising 5 planar surfaces as shown in FIG. 10 is an example of a partial cube.

As used herein, the phrase "wide angle lens" refers to a lens of a camera having an angle of view of 64 degrees or more.

As used herein, the phrase "axis of movement" refers to a direction in which movement can occur. For example, in an x, y, z coordinate system, x, y, and z are examples of axes of movement.

Exemplary Computing Environment

FIG. 1 is a diagram of an environment 100 in which one or more embodiments of the present disclosure can be practiced. The environment 100 includes a creative apparatus that supports various creative functions performed by users using one or more user devices, such as a user device 102A up to a user device 102N. The creative functions, for example, can enable users to view, create, and/or edit electronic content that has a surface or other appearance attribute that is based on reflectance properties determined using the devices and techniques described herein.

Each of the user devices is connected to a creative apparatus 108 via a network 106. Users of the user devices uses various products, applications, or services supported by the creative apparatus 108 via the network 106. The user devices correspond to various users. Examples of the users include, but are not limited to, creative professionals or hobbyists who use creative tools to generate, edit, track, or manage creative content, end users, administrators, users who use document tools to create, edit, track, or manage documents, advertisers, publishers, developers, content owners, content managers, content creators, content viewers, content consumers, designers, editors, any combination of these users, or any other user who uses digital tools to create, view, edit, track, or manage digital experiences.

Digital tool, as described herein, includes a tool that is used for performing a function or a workflow electronically. Examples of the digital tool include, but are not limited to, content creation tool, content editing tool, content publishing tool, content tracking tool, content managing tool, content printing tool, content consumption tool, any combination of these tools, or any other tool that can be used for creating, editing, managing, generating, tracking, consuming or performing any other function or workflow related to content. Digital tools include the creative apparatus 108.

Digital experience, as described herein, includes experience that can be consumed through an electronic device.

Examples of the digital experience include content creating, content editing, content tracking, content publishing, content posting, content printing, content managing, content viewing, content consuming, any combination of these experiences, or any other workflow or function that can be performed related to content.

Content, as described herein, includes electronic content. Examples of the content include, but are not limited to, image, video, website, webpage, user interface, menu item, tool menu, magazine, slideshow, animation, social post, comment, blog, data feed, audio, advertisement, vector graphic, bitmap, document, any combination of one or more content, or any other electronic content.

Examples of the user devices 102A-N include, but are not limited to, a personal computer (PC), a tablet computer, a desktop computer, a processing unit, any combination of these devices, or any other suitable device having one or more processors. Each user device includes at least one application supported by the creative apparatus 108.

It is to be appreciated that following description is now explained using the user device 102A as an example and any other user device can be used.

Examples of the network 106 include, but are not limited to, internet, local area network (LAN), wireless area network, wired area network, wide area network, and the like.

The creative apparatus 108 includes one or more engines for providing one or more digital experiences to the user. The creative apparatus 108 can be implemented using one or more servers, one or more platforms with corresponding application programming interfaces, cloud infrastructure and the like. In addition, each engine can also be implemented using one or more servers, one or more platforms with corresponding application programming interfaces, cloud infrastructure and the like. The creative apparatus 108 also includes a data storage unit 112. The data storage unit 112 can be implemented as one or more databases or one or more data servers. The data storage unit 112 includes data that is used by the engines of the creative apparatus 108.

A user of the user device 102A visits a webpage or an application store to explore applications supported by the creative apparatus 108. The creative apparatus 108 provides the applications as a software as a service (SaaS), or as a standalone application that can be installed on the user device 102A, or as a combination. The user creates an account with the creative apparatus 108 by providing user details and also by creating login details. Alternatively, the creative apparatus 108 can automatically create login details for the user in response to receipt of the user details. In some embodiments, the user is also prompted to install an application manager. The application manager enables the user to manage installation of various applications supported by the creative apparatus 108 and also to manage other functionalities, such as updates, subscription accounts and the like, associated with the applications. The user details are received by a user management engine 116 and stored as user data 118 in the data storage unit 112. In some embodiments, the user data 118 further includes account data 120 under which the user details are stored.

The user can either opt for a trial account or can make payment based on type of account or subscription chosen by the user. Alternatively, the payment can be based on a product or number of products chosen by the user. Based on payment details of the user, a user operational profile 122 is generated by an entitlement engine 124. The user operational profile 122 is stored in the data storage unit 112 and indicates entitlement of the user to various products or services. The user operational profile 122 also indicates type of user, i.e. free, trial, student, discounted, or paid.

The user then installs various applications supported by the creative apparatus 108 via an application download management engine 126. Application installers or application programs 128 present in the data storage unit 112 are fetched by the application download management engine 126 and made available to the user directly or via the application manager. In one embodiment, all application programs 128 are fetched and provided to the user via an interface of the application manager. In another embodiment, application programs 128 for which the user is eligible based on user's operational profile are displayed to the user. The user then selects the application programs 128 or the applications that the user wants to download. The application programs 128 are then downloaded on the user device 102A by the application manager via the application download management engine 126. Corresponding data regarding the download is also updated in the user operational profile 122. An application program 128 is an example of the digital tool. The application download management engine 126 also manages the process of providing updates to the user device 102A.

Upon download, installation and launching of an application program, in one embodiment, the user is asked to provide login details. A check is again made by the user management engine 116 and the entitlement engine 124 to ensure that the user is entitled to use the application program. In another embodiment, direct access is provided to the application program as the user is already logged into the application manager.

The user uses one or more application programs 128 to create one or more projects or assets. In addition, the user also has a workspace within each application program. The workspace, as described herein, includes setting of the application program, setting of tools or setting of user interface provided by the application program, and any other setting or properties specific to the application program. Each user has a workspace.

The application program data 130 includes one or more assets 140. The assets 140 can be a shared asset which the user wants to share with other users or which the user wants to offer on a marketplace. The assets 140 can also be shared across multiple application programs 128. Each asset includes metadata 142. Examples of the metadata 142 include, but are not limited to, font, color, size, shape, coordinate, a combination of any of these, and the like. In addition, in one embodiment, each asset also includes a file. Examples of the file include, but are not limited to, an image 144, text 146, a video 148, a font 150, a document 152, a combination of any of these, and the like. In another embodiment, an asset only includes the metadata 142.

The application program data 130 also include project data 154 and workspace data 156. In one embodiment, the project data 154 includes the assets 140. In another embodiment, the assets 140 are standalone assets. Similarly, the workspace data 156 can be part of the project data 154 in one embodiment while it may be standalone data in another embodiment.

In some embodiments, the user interaction with the application programs 128 is also tracked by an application analytics engine 158 and stored as application analytics data 160. The application analytics data 160 includes, for example, usage of a tool, usage of a feature, usage of a workflow, usage of the assets 140, and the like. The application analytics data 160 can include the usage data on a per user basis and can also include the usage data on a per tool basis or per feature basis or per workflow basis or any other basis. The application analytics engine 158 embeds a piece of code in the application programs 128 that enables an application program to collect the usage data and send it to the application analytics engine 158. The application analytics engine 158 stores the usage data as the application analytics data 160 and processes the application analytics data 160 to draw meaningful output. For example, the application analytics engine 158 can draw an output that the user uses "Tool 4 " a maximum number of times. The output of the application analytics engine 158 is used by a personalization engine 162 to personalize the tool menu for the user to show "Tool 4 " on top. Other types of personalization can also be performed based on the application analytics data 158. In addition, the personalization engine 162 can also use the workspace data 156 or the user data 118 including user preferences to personalize one or more application programs 128 for the user.

In some embodiments, the application analytics data 160 includes data indicating status of project of the user. For example, if the user was preparing an article in a digital publishing application and what was left was publishing the prepared article at the time the user quit the digital publishing application then the application analytics engine 158 tracks the state. Now when the user next opens the digital publishing application on another device then the user is indicated the state and the options are provided to the user for publishing using the digital publishing application or any other application.

The creative apparatus 108 also includes a community engine 164 which enables creation of various communities and collaboration among the communities. A community, as described herein, includes a group of users that share at least one common interest. The community can be closed, i.e. limited to a number of users or can be open, i.e. anyone can participate. The community enables the users to share each other' s work and comment or like each other's work. The work includes the application program data 140. The community engine 164 stores any data corresponding to the community, such as work shared on the community and comments or likes received for the work as community data 166. The community data 166 also includes notification data and is used for notifying other users by the community engine in case of any activity related to the work or new work being shared. The community engine 164 can provide collaborative workflows to the user. For example, the user can create an image and can request for some expert opinion or expert editing. An expert user can then either edit the image as per the user liking or can provide expert opinion. In collaborative workflows, each of a plurality of users are assigned different tasks related to the work.

The creative apparatus 108 also includes a marketplace engine 168 for providing a marketplace to one or more users. The marketplace engine 168 enables the user to offer an asset for sale or use. The marketplace engine 168 has access to the assets 140 that the user wants to offer on the marketplace. The creative apparatus 108 also includes a search engine 170 to enable searching of the assets 140 in the marketplace. The search engine 170 is also a part of one or more application programs 128 to enable the user to perform search for the assets 140 or any other type of the application program data 130. The search engine 170 can perform a search for an asset using the metadata 142 or the file.

Figure 2:
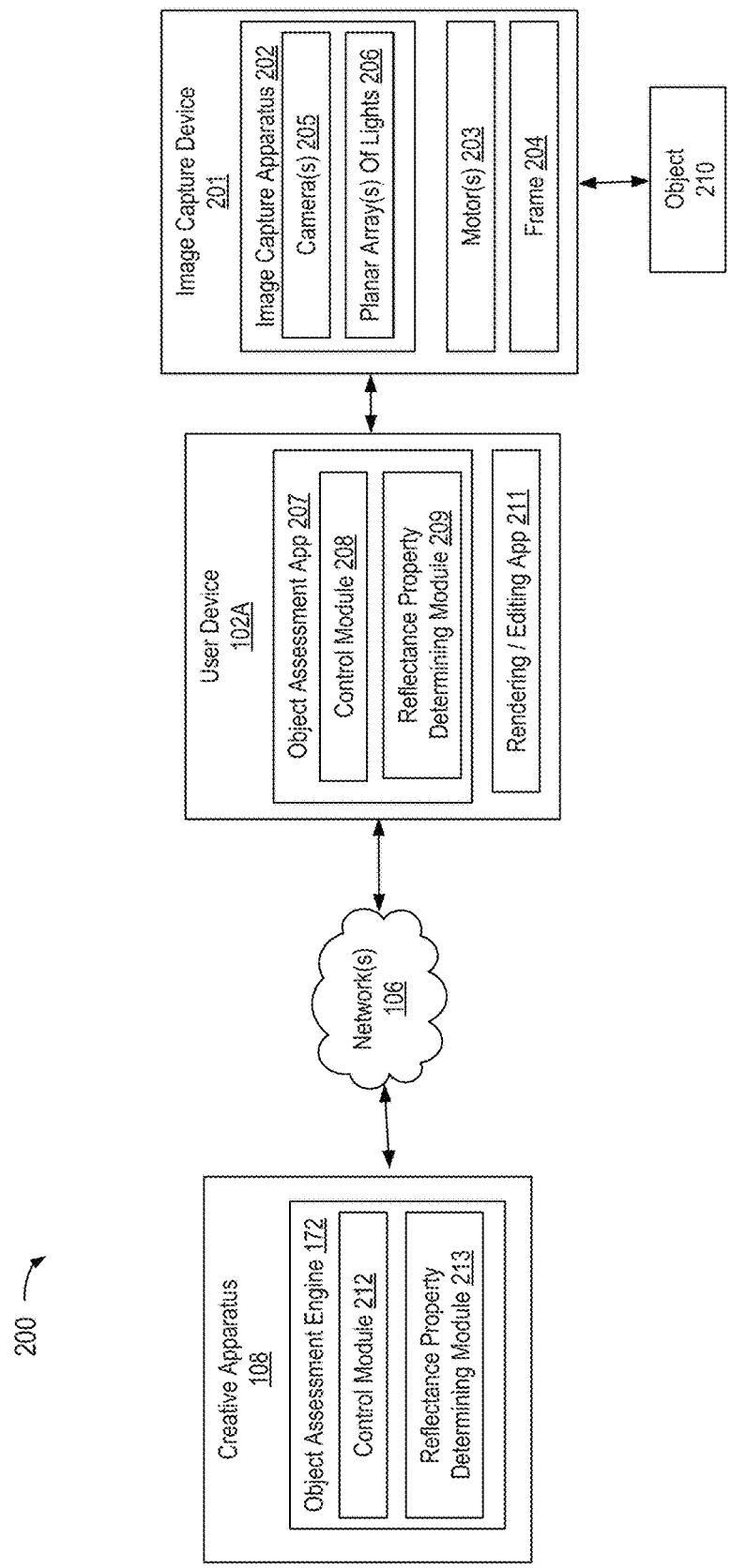
FIG. 2 is a diagram illustrating exemplary devices for capturing images with variable image capture conditions to determine reflectance properties of an object.

The creative apparatus 108 also includes an object assessment engine 172 that enables users to determine reflectance properties determined using the devices and techniques described herein. In one embodiment, the object assessment engine 172 remotely control of a user's image capture device. In another embodiment, the object assessment engine provides an application for use on a user device 102A. FIG. 2 illustrates this exemplary embodiment.

It is to be appreciated that the engines and working of the engines are described as examples herein and the engines can be used for performing any step in providing a digital experience to the user.

Embodiments of the invention provide techniques, systems, and computer-readable mediums with stored instructions that enable capturing images and/or using the captured images to determine reflectance properties of an object. The functions involved in these embodiments of the invention generally involve image capture, control of the image capture, and determining reflectance properties. The image capture generally involves capturing images of the object under different lighting conditions using a planar surface of lights. These functions are performed by various structural components including but not limited to an image capture apparatus that includes a camera and planar array of lights, one or more motors, and/or a frame with supports that support the image capture apparatus and motor relative to an object so that images can be taken of the object. With respect to control of the image capture and determining the reflectance property, these functions are generally implemented on one or more computing devices that use one or more processors to execute algorithms of one or more operations defined in stored instructions. The computing devices that perform these control and determining functions can be integrated into a device used to capture the images, can be separate at the same physical location (e.g., in the same room, building, etc.) as the image capturing device, or can be located remotely from the image capturing device. For example, the computing devices that perform the control and/or determining functions can be located on a remote computing devices, such as on creative apparatus 108 of FIGS. 1 and 2. The operations of various exemplary algorithms that can be employed to perform these functions are discussed throughout this specification.

FIG. 2 is a diagram illustrating a system 200 for capturing images with variable image capture conditions to determine reflectance properties of an object. The image capture device 201 is controlled by the user device 102A or the creative apparatus 108 to capture images. The user device 102A or the creative apparatus 108 identifies image capture conditions, determines camera and light configuration for the image capture device 201 to capture images under those image capture conditions, and then controls the image capture device to capture the image under those camera and light configurations. In one example, identifying a set of image capture conditions for capturing a set of images of the object using the image capture device 201 involves identifying a set of different camera directions selected to capture images of the object from different directions relative to the object and then selecting light directions to be used when capturing multiple images for each of the camera directions. For example, thirty six camera directions can be identified and, for each camera direction, three hundred and sixty light directions can be identified. The image capture conditions of the image capture device 201 are then determined based on the image capture conditions. For each image capture condition, a camera position and light position are determined to provide the desired camera direction and light direction. The user device 102A or the creative apparatus 108 controls the image capture device 201 to capture images of the object using these different camera and light configurations. The captured images, taken under the variable image capture conditions, can then be used to determine reflectance properties of the object.

The image capture device 201 includes an image capture apparatus 202, one or more motors 203, and a frame 204. The image capture apparatus 202 includes one or more cameras 205 and one or more planar arrays of lights 206. In an alternative implementation, the one or more cameras 205 and the one or more planar arrays of lights 206 are separated from one another. For example, the camera in such an embodiment can be moved independently from the one or more planar arrays of lights 206.

The one or more planar arrays of lights 206 provide lights used to illuminate an object 210 while the one or more cameras 205 capture images of the object 210. The one or more planar arrays of lights 206 can form various shapes to provide lighting from various directions relative to the object 210. In one example, the one or more planar arrays of lights provide a flat surface of lights above the object 210 as illustrated in FIGS. 3-7.

In another example, the one or more planar arrays of lights 206 provide a partial-cube configuration with lights on the inside surfaces of the partial cube. The partial cube has one open side (e.g., the bottom) so that the lights can illuminate the object 210 positioned near that opening from different directions. In such a partial cube-configuration, the partial cube has a planar surface (inside top) and side surfaces (inside sides) extending orthogonally from the planar surface that include lights that provide light inwardly toward the object 210. FIGS. 8-10 provide examples of partial-cube configurations.

In certain embodiments of the invention, the lights of the planar array of lights 206 are light emitting diodes (LEDs). In one embodiment, each of the LEDs has a built-in controller for individually illuminating the respective LED based on receiving lighting instructions. The LEDs can be connected to one another to receive power and/or lighting instructions or the LEDs can individually receive power from a power source [not shown] and/or instructions from a control module, such as control module 208 or 212, as explained below. In certain embodiments of the invention, the LEDs within a planar array of LEDs are serially connected to one another to receive power and/or lighting instructions. In embodiments that use multiple planar arrays of LEDs, the planar arrays can similarly be serially connected to one another. For example, two planar arrays of LEDs can be serially connected to one another such that a single serial connection controls the LEDs of both of the planar arrays. The serial connection of LEDs and/or planar arrays of LEDs to one another as well as using individual controls to control the individual LEDs reduces the complexity of the image capture apparatus 201 and the number of connections or wires that might otherwise be required to use and control the same number of lights. For example, a single power connection and/or a single data connection can be connected to the lights. Moreover, off-the-shelf planar arrays of LEDs with built-in individual LED controllers can be used and combined to limit the complexity, assembly time, weight, and otherwise make the image capture device easier and less expensive to produce and more efficient and effective in operation. Repair of the image capture device 202 in such embodiments, can similarly be made easier and less expensive through the use of off-the-shelf planar arrays of LEDs with built-in individual LED controllers.

Figure 4:
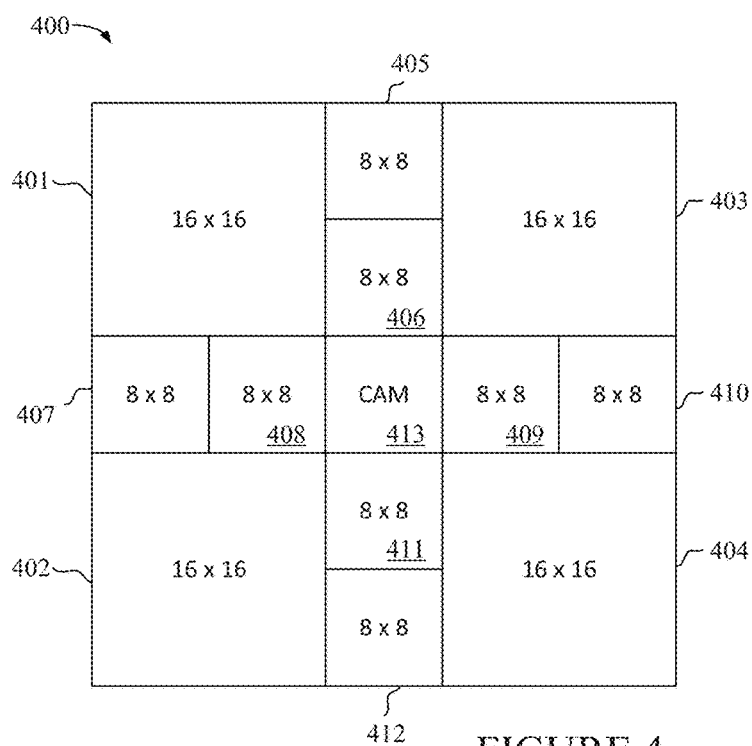
FIG. 4 is a bottom view of another image capture apparatus that includes multiple planar arrays of lights connected to one another.

The shape of the image capture apparatus 202 can be based on the shape of off-the-shelf arrays of LED components that are used and/or the shape and image capture properties of the camera. For example, if the image capture apparatus provides a flat, square planar surface with no curves or sizes, the dimensions of that surface can be configured based on the dimensions of combinations of off-the-shelf arrays of LEDs that are combined to form the surface. FIG. 4 provides an example of a planar surface having dimensions configured based on dimensions of the planar arrays of LEDs. Similarly, if the image capture apparatus uses a partial cube configuration for the lights, the dimensions of the sides of the partial cube can be configured based on dimensions of the planar arrays of LEDs. Sizing the lighting surfaces of the image capture apparatus 202 based on dimensions of off-the-shelf planar arrays of LEDs can limit the complexity, assembly time, weight, size, and otherwise make the image capture device easier and less expensive to produce and more efficient and effective in operation. In one embodiment, an image capture apparatus comprises one or more flat panels of metal, plastic, or wood that are molded, cut, or otherwise created to have a particular width, length, and depth dimensions. The one or more lighting arrays are then affixed to the one or more flat panels via an adhesive, molding, one or more attachment members, or any other appropriate attachment technique. The sides of a multi-sided structure such as a partial cube configuration are attached to one another via screws or other mechanical connections, an adhesive, molding, or any other appropriate attachment technique. In one embodiment of a partial cube configuration, the sides are configured to detach and reattach to a flat upper surface. In an alternative embodiment, a multi-side structure such as a partial cube configuration is formed as a single piece, for example, by molding and/or bending a sheet of material to an appropriate shape.

The image capture apparatus 202, by using one or more planar arrays of lights, is able to provide a much higher density of lights than prior hemisphere (i.e., non-planar, dome-shaped) light assemblies. For example, rather than being limited to twenty or so lights like certain prior devices, embodiments of the invention use hundreds or even thousands of lights. One embodiment of the invention uses 4,096 lights. Moreover, using dense arrays of programmable LEDs that are inexpensive and/or available off-the-shelf, allows the higher density of lights to be provided without unduly increasing the complexity of the device. The higher density of lights provides much higher angular illumination resolutions. This higher angular illumination resolution is especially valuable for objects that have certain materials such as sparkly materials. Sparkly materials have small facets that catch the light at only particular angles. A very high resolution is required to characterize those materials accurately. Use of a partial cube configuration in certain embodiments of the invention can further enhance the angular resolution by providing additional lighting conditions for capturing images of an object.

In one embodiment of the invention, the lights of the one or more planar arrays of lights are high-frequency LEDs, for example, that illuminate at 20 kHz. Using high frequency LEDs avoids a possible flicker effect that could show up as banding on images of the object 210 captured by the one or more cameras 205. One embodiment of the invention uses red-green-blue (RGB) LEDs. Another embodiment of the invention uses red-green-blue-white (RGBW) LEDs to provide enhanced spectral quality. Other embodiments of the invention use organic LEDs such as LEDs printed on flat sheets. Use of organic LEDs can enable thousands or even millions of pixels to provide light to illuminate the object 210. In one embodiment, a planar sheet of LEDs (such as organic LEDs) is curved along one axis to provide a cone, cylinder, or arched structure for providing light to illuminate the object 210.

The one or more cameras 205 include an electronic sensor or photographic film onto which images of the object 210 are recorded. The one or more cameras 205 will generally include a lens through which light from the object 210 is received for capture. In one embodiment of the invention, the lens is a wide angle lens having an angle of view of 64 degrees or more. Using a wide angle lens can reduce the number of cameras needed to capture an image of the object 210 from diverse camera directions. In one embodiment of the invention, rather than having multiple cameras viewing the surface of the object 210 from different viewpoints, the surface is captured by a single (or small number of cameras) that are able to both capture the surface head on but also, when positioned to the side of the object, from the periphery. While a wide angle lens may have less linear resolution than a narrow angle lens, the overall resolution of the object that is obtained is still very accurate. Moreover, the image capture device 201 can be configured so that the one or more cameras 205 are relatively close to the object 210, e.g., less than 24 inches, 18 inches, 12 inches, etc. Being relatively close to the object 210 at least partially compensates for the lack of linear resolution of a wide angle lens.

The one or more cameras 205 are connected to a power source [not shown]. For example, the image capture device 201 can include a battery [not shown] and/or a connection [not shown] to an external power source such as an electrical power outlet or USB power connection. Similarly, the one or more cameras 205 are connected to a computing device such as user device 102A or creative apparatus 108 to receive instructions regarding capturing images and/or to provide images that are captured. For example, the one or more cameras 205 can receive instructions from control module 208 and/or control module 212 and/or provide images to reflectance property determining module 209 or reflectance property determining module 212. In certain embodiments of the invention, the one or more cameras 205 are further configured to zoom, focus, rotate, or otherwise change based on instructions, for example, received from control module 208 and/or control module 212. In another embodiment, the one or more cameras 205 are configured to move closer or further away from the object 210 to account for depth variations in the object. For example, a camera can be moved closer when capturing images of a lower portion of the object 210 and moved further away when capturing images of a higher portion of the object 210.

The one or more motors 203 are configured to move the image capture apparatus 202 (i.e., the one or more cameras 205 and/or the one or more planar arrays of light 206) relative to object 210. In one example, a first motor of the one or more motors 203 is configured to move the image capture apparatus 202 laterally above the object 210 in an "x" direction, a second motor is used to move the image capture apparatus 202 laterally above the object 210 in an "y" direction, and a third motor is configured to move the image capture apparatus 202 up and down above the object 210 in an "z" direction. In other embodiments of the invention, a single motor is used to move the image capture apparatus 202 in multiple directions. In other embodiments of the invention, the one or more motors 203 move the apparatus in only one or two directions. In other embodiments of the invention, the one or more motors 203 translated and/or rotate the image capture apparatus 202 to position the lights relative to the object 210. The one or more motors can allow movement of the image capture apparatus with more degrees of freedom that prior devices. Using off the shelf motors to move the camera and/or light assembly can reduce the complexity and cost of the image capture device 201. In one example, the image capture device 201 uses a relatively inexpensive, off-the-shelf x, y, z, gantry with three motors that can move the one or more camera 205 and/or one or more planar arrays of lights 206 along three axis of movement to enable a large number of image capture conditions. This additional freedom of movement can be particularly advantageous in capturing images of deep objects such as sculptures.

The one or more motors 203 are connected to a power source [not shown]. For example, the image capture device 201 can include a battery [not shown] and/or a connection [not shown] to an external power source such as an electrical power outlet. Similarly, the one or more motors 203 are connected to a computing device such as user device 102A or creative apparatus 108 to receive instructions regarding moving the image capture apparatus 202. For example, the one or more motors 203 can receive instructions from control module 208 and/or control module 212. The motors 203 can similarly respond to instructions with confirmation, acknowledgements, and other appropriate responses in certain embodiments.

The frame 204 provides structural support and/or stability for the image capture apparatus 202 and one or more motors 203. The frame 204 includes supports such as legs that extend to an external feature, such as the underlying floor, to support the one or more motors 203 and image capture apparatus 202 above the object 202. The frame 201 also supports the object 210 in one embodiment of the invention. In one embodiment of the invention, the legs extend outward away from the object 201 and downward to a floor surface to support the one or more motors 203 and image capture apparatus 202 above the object 210. The outward extension of such legs provides a greater range of movement. Outwardly extending leg supports can be particularly advantageous in embodiments in which the one or more planar arrays of lights 206 are on a partial cube configuration. The outwardly extending legs increase the range of motion of the partial cube configuration. Moreover, use of the outwardly extending support legs allows an off-the-shelf movement assembly, such as a computer numeric control (CNC) machine (e.g., of motors, rails, etc.) or off-the shelf x, y, z gantry, to be used to move the image capture apparatus 202 by enabling an extended range of motion to capture the images of the object 210. The legs can include adjustable feet to facilitate leveling of the device.

The user device 102A is a computing device with an object assessment application 207 and a rendering/editing application 212. The object assessment application 207 includes a control module 208 and a reflectance property determining module 209. The control module 208 controls the image capture device 201 to capture images of object 210 from different camera positions and under different lighting conditions. For example, the control module 208 can send an instruction for the one or more motors 203 to move the image capture apparatus 202 to a particular position relative to the object 204, a lighting instruction for the planar array of lights 206 to turn on a particular light or combination of lights, while leaving the rest of the lights off, and a capture instruction to the camera 205 to capture an image of the object 210 from that position and under the light from the selected light or combination of lights.

The reflectance property determining module 209 receives images of the object 210 from various camera positions and lighting conditions and uses the images to determine reflectance properties. In one embodiment of the invention, the reflectance property determining module 209 receives images and uses the images to determine a BDRF. In this way, the object assessment app 207 is able to determine a spatially varying BDRF for an object using a device that is relatively inexpensive, efficient, effective, and otherwise better than prior devices. For example, the object assessment app 207 can controls the image capture device 201 to capture images of an object 210 that has gold leaf in one place, matt paint in another place, and a sparkly texture in another place. The object assessment app 207 uses the captured images to determine a BDRF for the object that allows the appearance of the object to be realistically represented in renderings of the object 210.

The user device 102A includes a rendering/editing app 212 that renders a representation of the object 210 based on the determined BDRF. For example, the representation can include a surface that has an appearance determined using the BDRF in various locations. For example, a rendering of a three dimensional (3D) model of the object can include a surface that is determined based on the BDRF. In this example, a rendering of the 3D model uses a viewing direction, lighting direction, and the BDRF to determine how the surface will appear in the representation of the model. In the above example, a portion of the surface may appear like gold leaf, another portion may appear like matted paint, and another surface may have a sparkly texture. The rendering/editing app 212, in one embodiment of the invention, provides editing functions that allows a user to edit the 3D model or the appearance of a rendering of the 3D model. For example, the user may reshape, resize, resurface, create, delete, and otherwise make changes to items in the 3D model and/or a rendering of the 3D model.

The object assessment and rendering/editing functions described above with respect to user device 102A are implemented locally (e.g., in the same room, building, complex, etc.) to the image capture device 201. For example, the user device 102A can connect to the image capture device via a wired or wireless communications connection including, but not limited to, through a communications cable, a local area network, a wireless area network, etc. In one embodiment of the invention, the user device 102A, or one or more of the applications or modules of the user device 102A, is integrated into image capture device 201.

In one embodiment of the invention, object assessment and rendering/editing functions described above with respect to user device 102A are implemented remotely from the image capture device 201 and communicate with the image capture device 201 via network(s) 106. For example, creative apparatus 108 (FIGS. 1 and 2), can include an object assessment engine 172, that includes a control module 212 and a reflectance property determining module 213 that perform similar functions to those of control module 208 and reflectance property determining module 209, respectively, from a remote location.

Figure 3:
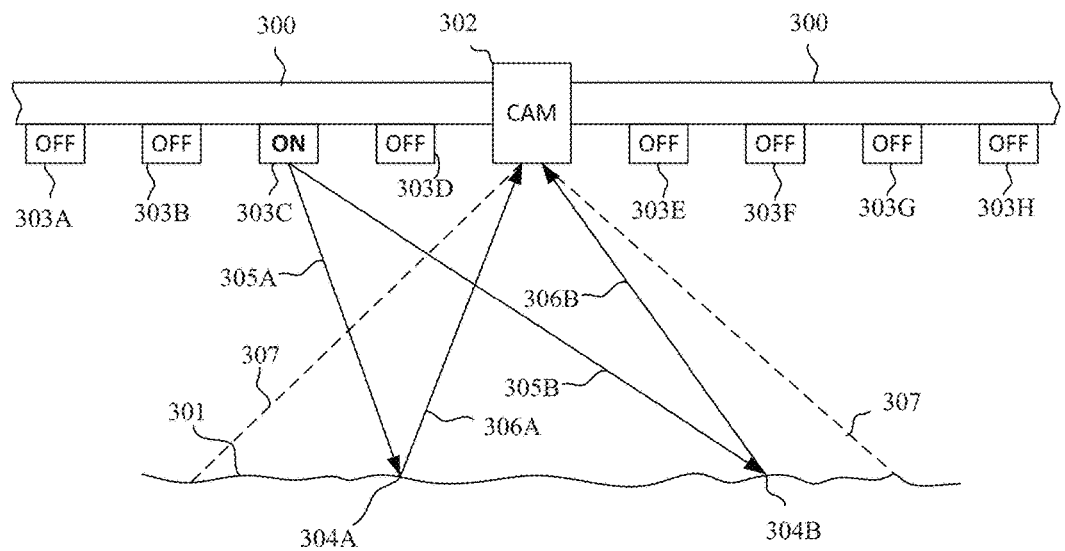
FIG. 3 is a cross sectional view of an exemplary image capture apparatus capturing an image using a selected light of a planar array of lights.

FIG. 3 is a cross sectional view of an exemplary image capture apparatus using a camera 302 to capture an image of an object 301 using a selected light of a planar array of lights. In this example, the planar array of lights includes lights 303A-H positioned on planar surface 300. The camera 302 is positioned to extend through a hole in the planar surface 300. In this example, only light 303C is on and the other lights 303A-B and 303D-H are off. While only light 303C is on, the camera 302 captures an image of the object 301. Specifically, the camera 302 captures an image of the object 301 within the cone 307. Cone 307 will differ depending on the angle of the lens used by the camera 302.

Light from the light 303C reflects off of the various positions along the object 301 to the camera 302. For example, light from the light 303C reflects off of position 304A to the camera 302 and reflects off of position 304B to the camera. The light that the camera 302 captures will depend on the material and the particular locations. For example, a sparkly material at position 304A will reflect light differently than a non-sparkly material.

Multiple images of the object 301 are captured using different ones of the lights 303A-303H to provide information that is used to determine how to represent the reflectance properties of the object 301 in the various positions, e.g., at position 304A, 304B, etc. on the surface of the object 301. Moreover, additional images of the object 301 are obtained by repeating the image captures with the camera and lights at different positions relative to the object 301. For example, the camera and lights could be moved a few inches to the right and additional images captured using different ones of lights 303A-H to illuminate the object 301. In this way, camera 302 captures images that are used to determine how to represent the reflectance properties of the object 301 for a variety of lighting and viewing conditions.

FIG. 4 is a bottom view of another image capture apparatus of multiple planar lighting arrays connected to one another. In this example, a planar surface 400 is created by combining planar arrays of lights of predetermined sizes, i.e., planar arrays 401, 402, 403, 404 having 16 lights by 16 lights and planar arrays 405, 406, 407, 408, 409, 410, 411, 412 having 8 lights by 8 lights. These planar arrays of lights 401-412 can be off-the-shelf components. In the example of FIG. 4, the length and width dimensions of the planar surface 400 are configured based on the dimensions of the planar arrays of lights 401-412 and/or the shape and image capture properties of the camera. Specifically, the width of the planar surface 400 is based on using two 16×16 planar arrays of lights and one 8×8 planar array of lights across the planar surface. Similarly, the length of the planar surface 400 is based on using two 16×16 planar arrays of lights and one 8×8 planar array of lights across the planar surface. The planar surface 400 can include an opening [not shown] configured to fit camera 413.

Figure 5:
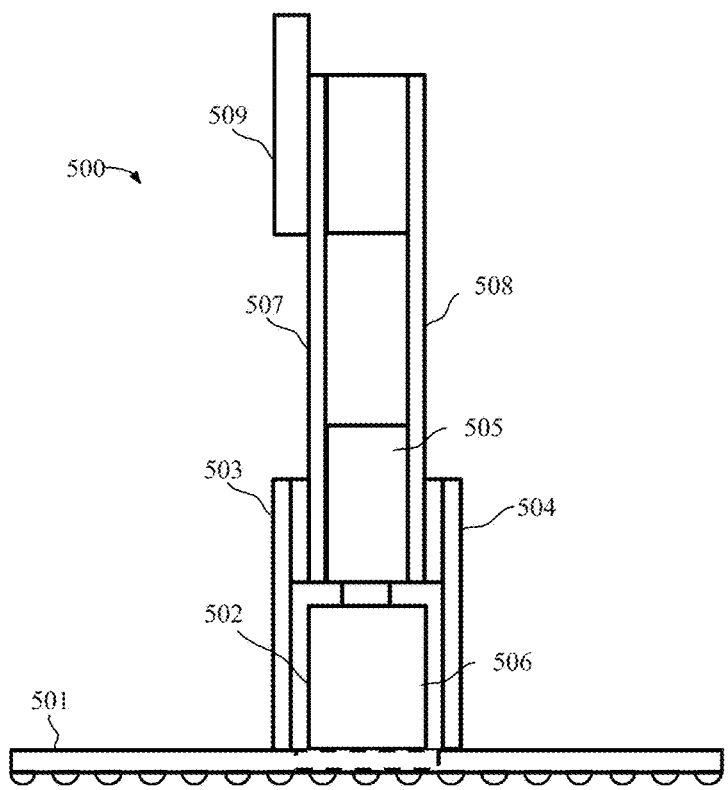
FIG. 5 is a side view of an exemplary image capture apparatus for capturing images with variable image capture conditions to determine reflectance properties of an object.

FIG. 5 is a side view of an exemplary image capture apparatus 500 for capturing images with variable image capture conditions to determine reflectance properties of an object. In this example, the image capture apparatus 500 includes a planar array of lights 501 and a camera 502. Support members 503, 504 connect the planar array of lights 501 to an upper portion 505 of the camera 502 without interfering with a lens 506 of the camera 502. For example, the lens 506 of the camera 502 can rotate or move to focus or otherwise adjust the camera since the support members 503, 504 connect to the upper portion 505 of the camera 502. Supports 507 and 508 connect the camera 502 and array of lights 501 to an attachment member 509 that is configured to attach the image capture apparatus to other components (e.g., motor(s), frame, etc.) of an image capture device.

Figure 6:
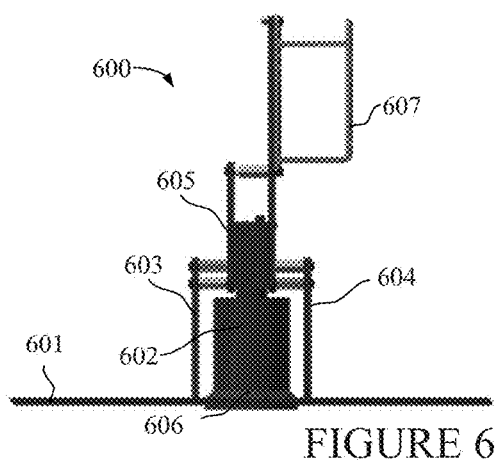
FIG. 6 is a side view of another exemplary image capture apparatus for capturing images with variable image capture conditions to determine reflectance properties of an object.
Figure 7:
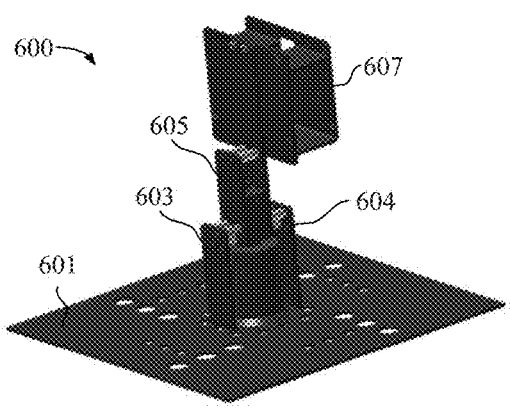
FIG. 7 is an isometric view of the exemplary image capture apparatus of FIG. 6.

FIG. 6 is a side view of another exemplary image capture apparatus 600 for capturing images with variable image capture conditions to determine reflectance properties of an object. FIG. 7 is an isometric view of the exemplary image capture apparatus 600 of FIG. 6. In this example, the image capture apparatus 600 includes a planar array of lights 601 and a camera 602. Support members 603, 604 connect the planar array of lights 601 to an upper portion 605 of the camera 602 without interfering with a lens 606 of the camera 602. An attachment member 607 is configured to attach the image capture apparatus 600 to other components (e.g., motor(s), frame, etc.) of an image capture device.

FIG. 8 is a cross sectional view of an exemplary image capture apparatus having a partial-cube shaped light assembly 800. In this example, the light assembly 800 includes planar lighting arrays that include lights 803A-P positioned on the inside surfaces of the partial-cube shaped light assembly 800. The camera 802 is positioned to extend through a hole in the planar surface 800. In use, one or more of the lights 803A-P is turned on to illuminate the object 801 while the camera 802 captures images of the object 801. The camera 802 is moved and different lights are illuminated to capture images of the object 801 from a variety of image capture conditions. The captured images are then used to determine reflectance properties of the object 801.

FIG. 9 illustrates surface 901, 902, 903, 904, 905 each having multiple connected planar lighting arrays. The surfaces 901-905 are configured to be combined as the sides of an exemplary image capture apparatus that has a partial-cube configuration. FIG. 10 is an isometric view of the exemplary image capture apparatus of FIG. 9 with the sides connected to one another in a partial-cube shaped light assembly. In this configuration, the bottom of the image capture apparatus is open so that lights on the inside of the partial-cube shaped light assembly, e.g., on the inside of surfaces 901-905 illuminate an object that is below or within the light assembly.

Figure 11:
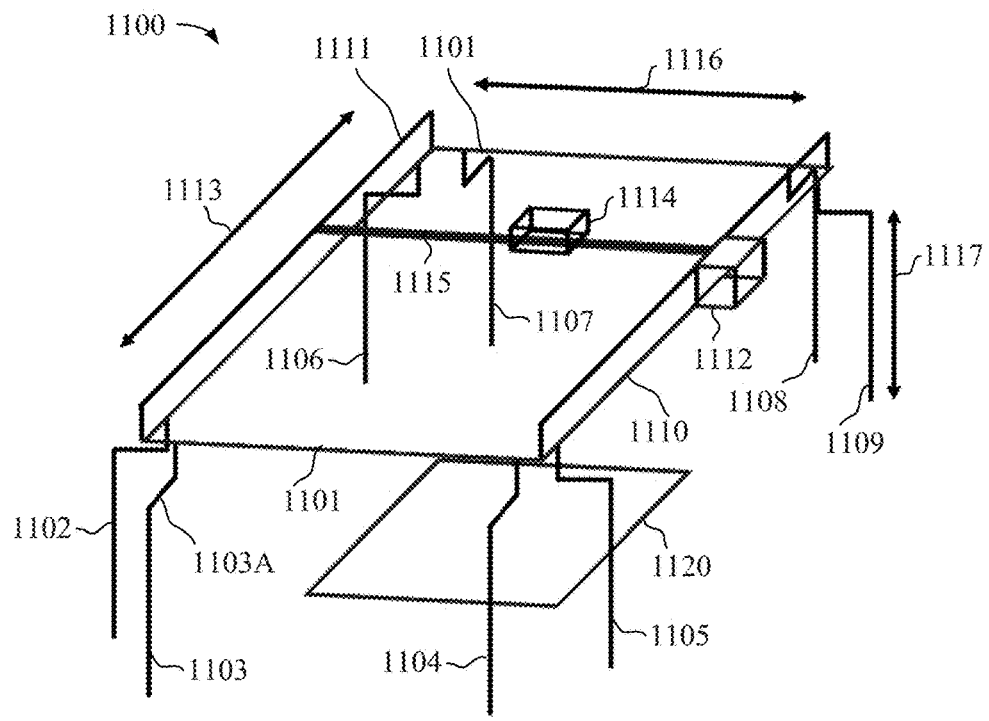
FIG. 11 is an isometric view of an exemplary frame and motors for supporting and moving an image capture apparatus.

FIG. 11 is an isometric view of an exemplary frame 1100 and motors 1112, 1114 for supporting and moving one or more lights and cameras. In this example the frame 1100 includes a frame top 1101 that is supported by legs 1102, 1103, 1104, 1105, 1106, 1107, 1108, 1109. Each of these legs 1102, 1103, 1104, 1105, 1106, 1107, 1108, 1109 includes a portion that allows the respective leg to extend outward away from the object 1120 that is being captured. For example, leg 1103 includes an outward extending portion 1103A that extends the leg 1103 away from the object 1103. These extensions enable the use of an off-the-shelf component such as a computer numeric control (CNC) machine to provide the motors 1112, 1114 and tracks that move the one or more lights and/or cameras. The extensions allow such an off-the-shelf component to be used to move the one or more lights and/or cameras by supporting the off-the-shelf component above the object while providing sufficient room for the off-the-shelf component to move the one or more lights and/or cameras without the legs interfering with that movement. The extensions of the legs 1102-1109 increase the range of movement of the lights and cameras. Motor 1112 is configured to move a bar 1115 in directions 1113 along supports rails 1110, 1111. Motor 1114 is configured to move in directions 1116 along bar 1115. An image capture apparatus can attach to motor 1114 to be moved by motor 1114 in direction 1116 and by motor 1112 in direction 1113. In one embodiment of the invention, three or more motors are used to move the image capture apparatus in direction 1113, direction 1116, and up and down. For example, motor 1114 can include an additional motor to move up and down.

Figure 12:
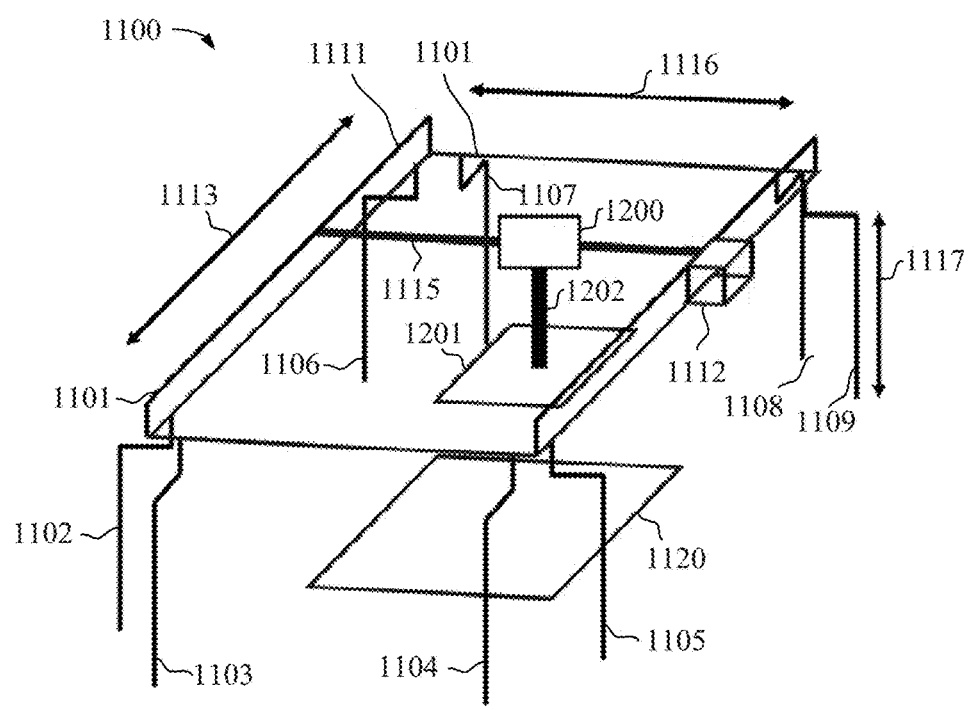
FIG. 12 is an isometric view of an exemplary device for capturing images with variable image capture conditions to determine reflectance properties of an object.

FIG. 12 is an isometric view of an exemplary device for capturing images with variable image capture conditions to determine reflectance properties of an object. The exemplary device includes the frame 1100 and motors 1112, 1114 of FIG. 11 with an image capture apparatus 1200 attached. The image capture apparatus 1200 includes a camera 1202 facing down capture images of object 1120 through a hole in light surface 1201. Light surface 1201 includes lights [not shown] facing down to individually (or in combination) illuminate the object 1120 while the camera 1202 captures images.

Exemplary Techniques for Determining Reflectance Properties of Objects

Figure 13:
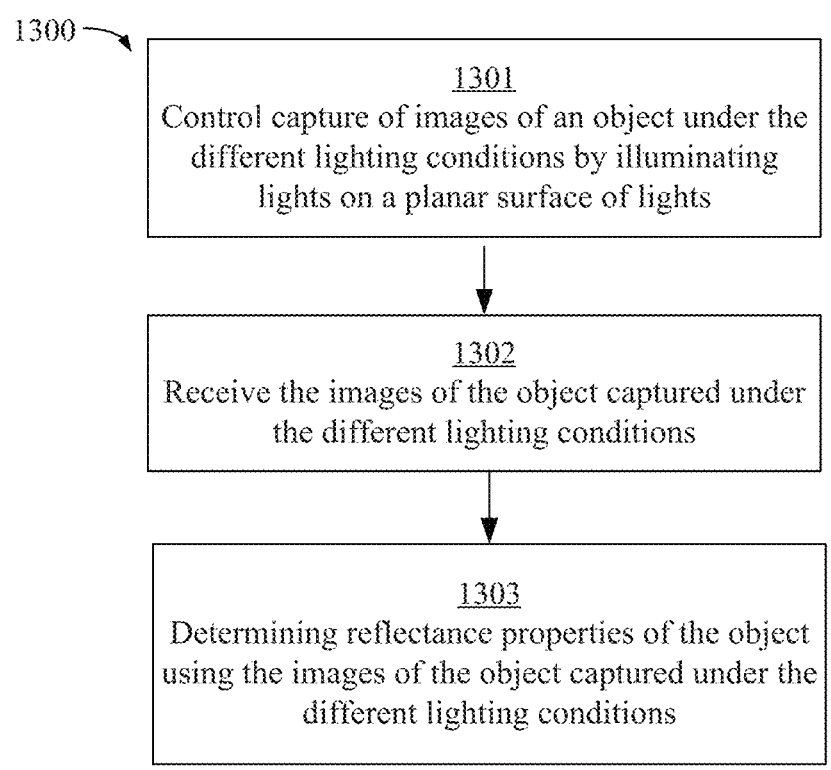
FIG. 13 is a flow chart illustrating an exemplary technique for determining reflectance properties of an object based on images captured with variable image capture conditions.

FIG. 13 is a flow chart illustrating an exemplary technique 1300 for determine reflectance properties of an object based on images captured with variable image capture conditions. The exemplary technique 1300 can be implemented by user device 102A or creative apparatus 108, although other devices and configurations can also be implemented. The exemplary technique 1300 can be implemented by storing and executing instructions in a non-transitory computer-readable medium.

Technique 1300 involves controlling capture of images of an object under different lighting conditions by illuminating lights on a planar surface of lights, as shown in block 1301. Controlling the capture of images of the object can involve controlling the lights to illuminate lights individually, in strips, or in various other combinations. In embodiments that illuminate multiple lights simultaneously, the lighting characteristics of the lights can be represented as a basis function used in interpreting captured images of the object to determine the object's reflectance properties. The selection of lights to illuminate and the combination of lights to illuminate can be selected to achieve a desired level of resolution. For example, to facilitate faster processing, the control process can use larger blocks of lights and capture fewer images. The results will be obtained more quickly than if more images are taken using smaller grouping of lights or individual lights. The brightness of the lights can also be controlled to balance exposure time and resolution. The brightness of a number of lights illuminated at once can be reduced to avoid over-exposure of the image. The brightness of the lights can additionally or alternatively be adjusted to enable high-dynamic range capture of the appearance, by capturing a sequence of images for different light brightness values, and combining the results. This can prevent certain regions, such as highlights and sparkles, from clipping due to the max sensor brightness, while also properly capturing darker regions of the material for the same lighting configuration. In one example, the technique illuminates lights gradually while images are captured to capture images using lighting of different brightness values.

Figure 14:
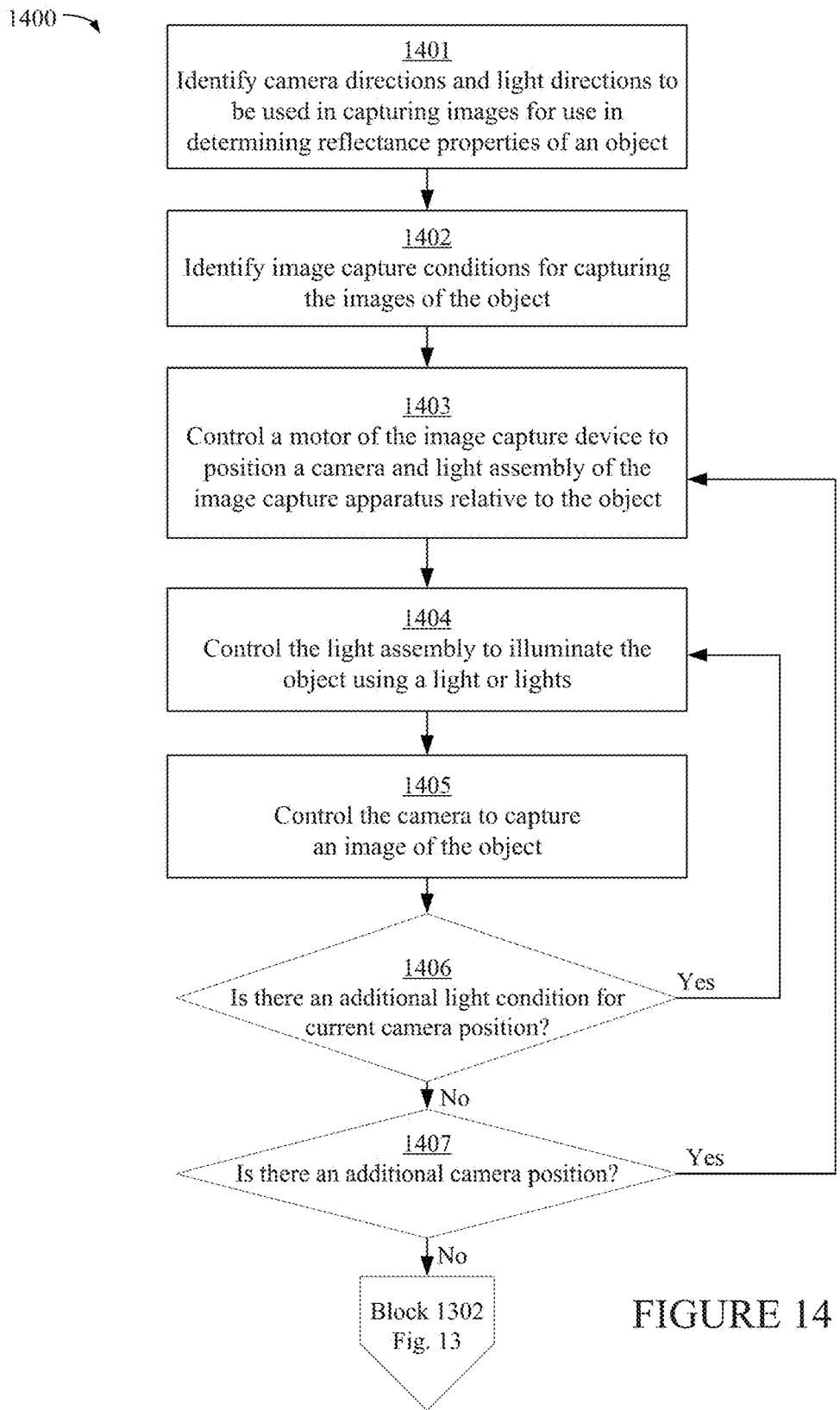
FIG. 14 is a flow chart illustrating an exemplary technique for controlling a device to capture images of an object using with variable image capture conditions.

FIG. 14 is a flow chart illustrating an exemplary technique 1400 for controlling a device to capture images of an object under variable image capture conditions. The exemplary technique 1400 can be implemented by user device 102A or creative apparatus 108, although other devices and configurations can also be implemented. The exemplary technique 1400 can be implemented by storing and executing instructions in a non-transitory computer-readable medium.

The technique 1400 involves identifying camera directions and light directions to be used in capturing images for use in determining reflectance properties of the object, as shown in block 1401. The camera directions and light directions are identified to provide a number of different views of the object from different camera directions and with the object illuminated from different light directions. The number and diversity of the different views is selected to be sufficient to determine the reflectance properties of the object with a specified resolution. Generally, the more views and the greater the differences amongst the views, the higher the resolution of the reflectance properties that can be determined. However, capturing images for a greater number of views can require more. Accordingly, the level of resolution can be selected to balance reflectance property resolution with speed. A particular object or circumstance may require a higher resolution that justifies the time required to capture a large number of views, while another object or circumstance require a lesser resolution that can be achieved with fewer views of the object. The resolution can be selected automatically or based on user input. For example, an initial scan of an object can provide a measure of the complexity, depth variation, and/or other characteristics of the object. These characteristics can be used to automatically select an appropriate reflectance property resolution to be obtained for the object. In one example, a higher resolution is selected for objects that are identified as including a spatially-varying material while a relatively smaller resolution is selected for objects without spatially-varying material.

User input can also be received to specify a resolution (e.g., low resolution, medium resolution, high resolution, etc.) that is used for a reflectance property determination for one or more specific objects or as a general preference for the user for all reflectance property determinations performed by the user. In one example, user input identifies whether the object includes spatially-varying material.

The camera directions and light directions can additionally or alternatively be identified based on constraints of the image capture device. For example, the possible camera angles may be limited based on the positions that a camera can take relative to the object and/or based on the type of lens of the camera. Thus, identifying the camera directions and light directions can thus involve identifying the range of possible camera directions and/or light directions that are possible for the image capture device. In another example, camera directions are selected based on evenly spaced camera positions, e.g., in a 4 by 4 grid of camera positions above the object. The even spacing of the camera positions in this example is selected to ensure that views of the object are captured from a variety of different camera directions relative to the object.

The technique 1400 further involves identifying image capture conditions for capturing the images of the object, as shown in block 1402. The image capture conditions specify different camera positions to capture the images of the object from the different camera directions. For example, this can involve determining a particular position of a camera relative to the object to capture an image of the object from a particular camera direction. The image capture conditions further specify illuminating the lights to capture the images with the object illuminated from the different lighting directions. For example, this can involve determining a position of a light assembly and selecting one or more particular lights to illuminate the object from a particular light direction. Multiple lights can be selected for simultaneous illumination, for example, to provide a block of lights or a line of lights, to provide various advantages. By using multiple lights together, a scene can be captured with short exposure times due to the large amount of light. Another technique involves using multiple lights to illuminate the object for a given image. Characteristics of the light provided by multiple lights can be assessed and used to determine the reflectance properties of the object. In one example, a line of lights is used to determine specular glints for a range of light positions. By moving the line in a sweep, a set of such images are captured, and then, by also capturing image sets for a second set of lines orthogonal to the first, highlight directions can be located with fewer images that would be otherwise required.

Identifying the image capture conditions can also involve determining groupings of image capture conditions. For example, all image capture conditions that include a common camera position can be grouped together and images captured for the grouping together. Using such groupings can minimize the amount of camera movement needed to achieve the camera and light configurations for the different image capture conditions.

The technique 1400 further involves blocks 1403-1407 to control the image capture device to capture images of the object to capture images of the object under the image capture conditions. In one example, the technique 1400 moves the camera of the image capture device to 16 different positions laterally above the object, e.g., in a 4 by 4 grid of positions. In each of the camera positions, a lighting sequence can be used to illuminate individual lights (or groups of lights) one after another in a sequence. Note that not every light on the image capture device needs to be used.

Blocks 1403-1407 illustrate an iterative process to control the image capture device to capture images of the object. This involves controlling a motor of the image capture device to position a camera and light assembly relative to an object, as shown in block 1403. For example, based on a first camera and light configuration, the technique can send a motor instruction to the motor or motors of the image capture device instructing the motor or motors to move the camera and light assembly so that the camera is at a desired location relative to the object. From this location, the camera will capture images of the object according to the corresponding camera direction. Multiple motors can be controlled, for example, to move the camera in different directions along one, two, or three axes of movement.

The technique 1400 further involves controlling the light assembly to illuminate the object using a light or lights, as shown in block 1404. The particular light or lights that are illuminated provide light from a light direction. In certain embodiments, a different, single light is illuminated while individual images of the object are captured. In other embodiments, multiple lights are used together to illuminate the object while individual images of the object are captured. Using more than one light, for example, a block of lights or a line of lights can result in images of the object that have information about multiple light directions. In one example, using images with multiple lights illuminating the object can reduce the number of images of the object needed to achieve a desired degree of reflectance property resolution.

The technique 1400 further involves controlling the camera of the image capture device to capture an image of the object, as shown in block 1405. The technique 1400 then determines whether there is an additional light condition for the current camera position relative to the object, as shown in block 1406. For example, if there is a group of 16 image capture conditions having the same camera position but different light positions, this can involve determining whether there are any additional image capture conditions in the group of 16 that still need to be used to capture images of the object. If so, the technique 1400 returns to block 1404 to control the light assembly to illuminate the object using a different light or lights.

Once there are no additional light conditions for the current camera position, the technique 1400 proceeds to determine whether there is an additional camera position to be used to capture images of the object, as shown in block 1406. For example, if there are 36 different camera positions in the camera and light configurations determined in block 1402, this can involve determining whether there are any additional camera positions that still need to be used to capture images of the object. If so, the technique 1400 returns to block 1403 to control the motor of the image capture device to position the camera and light assembly of the image capture apparatus in another position relative to an object.

Once there are no additional camera positions, the technique 1400 proceeds to return to block 1302 of FIG. 13.

The technique 1400 involve controlling the image capture device to capture multiple images of the object illuminated from multiple lighting directions using the camera in each of the multiple camera positions. In one embodiment of the invention, individual instructions are sent to control the motor, lights, and camera of the image capture device. In an alternative embodiment of the invention, instructions provided to control the motor to move the camera and/or lights, control the lights, and control the camera to capture images can be included in combined instructions and/or communications.

Returning to FIG. 13, after or while controlling the capture of images, technique 1300 further involves receiving the images of the object captured under the different lighting conditions, as shown in block 1302. For example, technique 1300 can be implemented in a computing device that is integrated with or in communication with an image capture device that performs the image capture. The captured images can be sent to the computing device via a wired or wireless communication network. In the case of a remote computing device, the images can be received via a non-local communications network such as the Internet.

Technique 1300 further involves determining reflectance properties of the object using the images of the object captured under the different lighting conditions, as shown in block 1303. In one embodiment of the invention determining the reflectance properties involves determining a BRDF based on the images. The BDRF provides a color of each pixel of a two dimensional (2D) or three dimensional (3D) representation of the object for a given light direction and a given camera direction. One example of determining a BDRF involves identifying a respective light used to light the each of the images, determining adjustments based on calibration information for the images, and determining the BDRF based on the images and the adjustments of the images.

Figure 15:
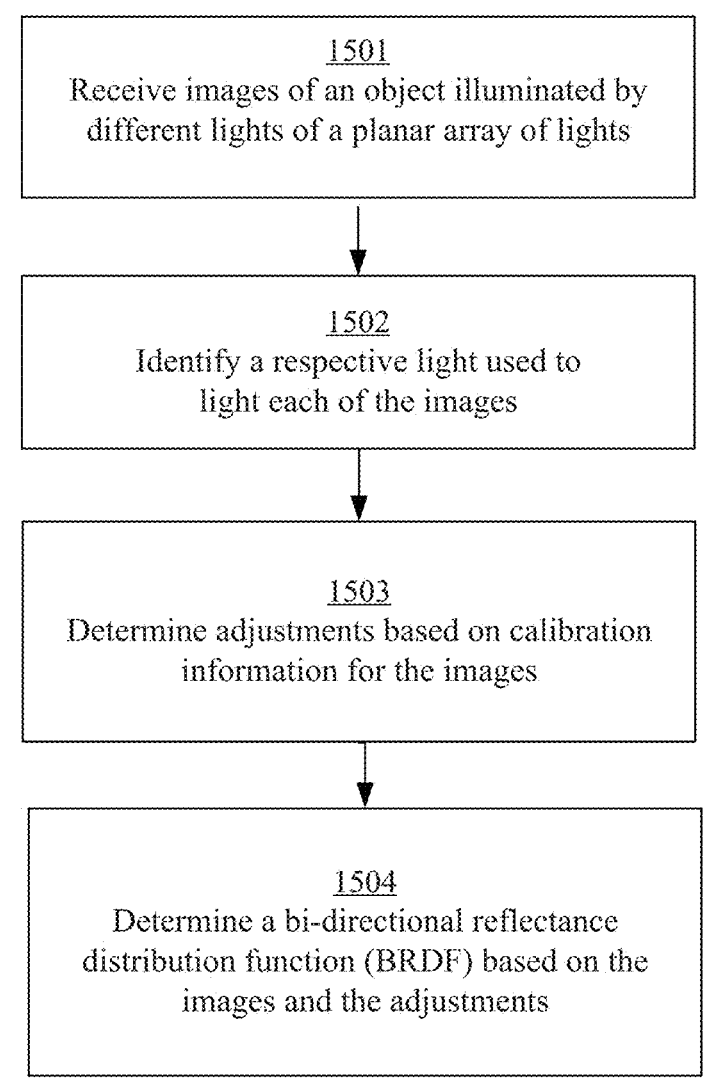
FIG. 15 is a flow chart illustrating an exemplary technique for using images of an object to determine a bi-directional reflectance distribution function.

FIG. 15 is a flow chart illustrating an exemplary technique 1500 for using images of an object to determine a bi-directional reflectance distribution function. The exemplary technique 1500 can be implemented by user device 102A or creative apparatus 108, although other devices and configurations can also be implemented. The exemplary technique 1500 can be implemented by storing and executing instructions in a non-transitory computer-readable medium.

Technique 1500 involves receiving images of an object illuminated by different lights of a planar array of lights, as shown in block 1502. As described with respect to FIG. 13, such images can be received through any appropriate wired or wireless communications.

Technique 1500 further involves identifying a respective light used to light each of the images, as shown in block 1502. Such information can be recorded by the image capture device while capturing the images and included in the images as metadata. For example, while the camera captures an image of the object, information about which lights are currently illuminated can be recorded. In an alternative implementation, a computing device controls the capture of the images by controlling which lights are on when the images are captured. The computing device records the information about which lights are on while the images are captured.

Technique 1500 further involves determining adjustments based on calibration information for the images, as shown in block 1503. In embodiments of the invention that use planar arrays of lights in which lights are not equidistant from the object being captured and potentially have other variations, a calibration process can be performed to account for lighting differences from the different lights. The calibration process can account for both the orientation of the lights and their distances from each surface point of an object.

One exemplary calibration technique involves using the device to create images of a diffuse surface such as a flat surface of white paint. Images of this surface are created using each of the lights in turn and the captured images are analyzed to determine calibration information for the device. For example, the brightness of each light relative to each location on the surface of the object can be determined. Such a calibration procedure generally need only be performed once for a given image capture device. In embodiments of the invention in which the camera and/or lights are moved up and down relative to an underlying object, the calibration process can additionally involve capturing images with the camera and lights at various distances above the object. Determining the calibration information can involve creating a lookup table or function that can be used to determine appropriate adjustments for given viewing directions, lighting conditions, and/or heights above the object. Calibrating the position of the lights relative to the camera can be achieved for some lights by imaging a front-surface planar mirror. Some of the lights will be seen directly via their reflection. This will help to calibrate the position of the lights, especially if this is done for two or more camera distances relative to the mirror. Alternatively, a curved or domed mirror could be used to see the reflection of some or all of the lights for one or more camera positions.

Technique 1500 further involves determining a BDRF based on the images and the adjustments, as shown in block 1504. For example, the adjustments can be used to adjust the pixel values in the images so that the pixel values represent pixel brightness for equivalent light brightness conditions. Thus, a value for a pixel for which the light was far away from the object may be increased based on that circumstance.

The BDRF or other reflectance information obtained using the embodiments of the invention can be used for a variety of purposes. The reflectance information can be used to provide more accurate representations of the surfaces of objects. The reflectance information can be used in 3D models in which surfaces have variable appearances for different viewing directions and lighting conditions. The reflectance information can be used in games, simulations, and movie productions in which objects are illuminated by light sources and viewed from various viewing directions. The appearance of surfaces in renderings in games, simulations, and movies can generally be made more realistic.

The devices and technique of embodiments of the invention also facilitate improved comparison of real world materials. For example, the devices and techniques can be used to compare the paint on a car with a batch of paint to determine how accurately the paints match with respect to reflectance properties.

The accurate determination of BRDF could also be used to control the composition and structure of objects being 3D-printed so that the resultant print would resemble the original object under a variety of viewing and illumination conditions.

Exemplary Computing Environment

Figure 16:
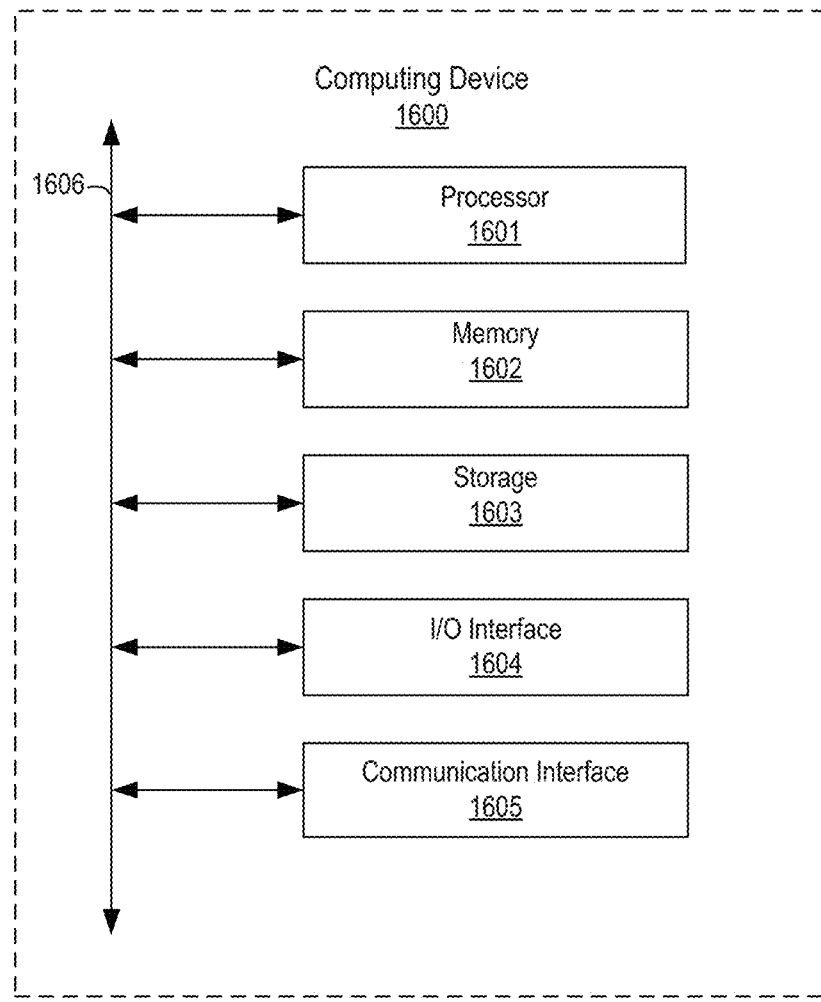
FIG. 16 is a block diagram depicting an example hardware implementation.

Any suitable computing system or group of computing systems can be used to implement the techniques and methods disclosed herein. For example, FIG. 16 is a block diagram depicting examples of implementations of such components. The computing device 1600 can include a processor 1601 that is communicatively coupled to a memory 1602 and that executes computer-executable program code and/or accesses information stored in memory 1602 or storage 1603. The processor 1601 may comprise a microprocessor, an application-specific integrated circuit ("ASIC"), a state machine, or other processing device. The processor 1601 can include one processing device or more than one processing device. Such a processor can include or may be in communication with a computer-readable medium storing instructions that, when executed by the processor 1601, cause the processor to perform the operations described herein.

The memory 1602 and storage 1603 can include any suitable non-transitory computer-readable medium. The computer-readable medium can include any electronic, optical, magnetic, or other storage device capable of providing a processor with computer-readable instructions or other program code. Non-limiting examples of a computer-readable medium include a magnetic disk, memory chip, ROM, RAM, an ASIC, a configured processor, optical storage, magnetic tape or other magnetic storage, or any other medium from which a computer processor can read instructions. The instructions may include processor-specific instructions generated by a compiler and/or an interpreter from code written in any suitable computer-programming language, including, for example, C, C++, C#, Visual Basic, Java, Python, Perl, JavaScript, and ActionScript.

The computing device 1600 may also comprise a number of external or internal devices such as input or output devices. For example, the computing device is shown with an input/output ("I/O") interface 1604 that can receive input from input devices or provide output to output devices. A communication interface 1605 may also be included in the computing device 1600 and can include any device or group of devices suitable for establishing a wired or wireless data connection to one or more data networks. Non-limiting examples of the communication interface 1605 include an Ethernet network adapter, a modem, and/or the like. The computing device 1600 can transmit messages as electronic or optical signals via the communication interface 1605. A bus 1606 can also be included to communicatively couple one or more components of the computing device 1600.

The computing device 1600 can execute program code that configures the processor 1601 to perform one or more of the operations described above. The program code can include one or more modules. The program code may be resident in the memory 1602, storage 1603, or any suitable computer-readable medium and may be executed by the processor 91 or any other suitable processor. In some embodiments, modules can be resident in the memory 1602. In additional or alternative embodiments, one or more modules can be resident in a memory that is accessible via a data network, such as a memory accessible to a cloud service.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure the claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

What is claimed is:

1. A system for capturing images for use in determining reflectance properties of an object, the system comprising:
   an image capture device comprising:
      a light assembly comprising a planar array of lights attached to a surface of the light assembly, the lights individually addressable and configured to illuminate the object based on receiving lighting instructions;
      a camera attached to the light assembly in a position relative to the lights to receive light from an object illuminated by the lights to capture images of the object, the camera configured to capture images of the object based on receiving camera instructions; and a motor attached to the light assembly and configured to move the lights and camera relative to the object based on receiving motor instructions; and a computing device with a processor configured to execute instructions to perform operations, the operations comprising:

identifying camera directions and light directions to be used in capturing images for use in determining reflectance properties of the object, wherein the camera directions and light directions are identified to provide a number of different views of the object from different camera directions and with the object illuminated from different light directions, the number and diversity of the different views sufficient to determine the reflectance properties of the object with a specified resolution;

identifying image capture conditions for capturing the images of the object, the image capture conditions specifying different camera positions to capture the images of the object from the different camera directions, the image capture conditions further specifying illuminating the lights to capture the images with the object illuminated from the different lighting directions; and providing instructions to the image capture device to position the lights and camera using the motor, illuminate the lights, and capture the images of the object under the image capture conditions using the camera.

2. The system of claim 1, wherein providing instructions to the image capture device comprises, for individual images:

determining a respective position of the camera and lights relative to the object and a respective selection of the lights to illuminate to capture the respective image from a respective camera direction and with the object illuminated from a respective light direction;

providing a motor instruction causing the motor to move the camera and lights into the respective position;

providing a lighting instruction to illuminate the respective selection of lights; and providing a camera instruction to capture the respective image.

3. The system of claim 1, wherein the planar array of lights comprises a planar array of light emitting diodes (LEDs), each of the LEDs having a built-in controller for individually illuminating the respective LED based on receiving the lighting instructions, each of the LEDs serially connected to one or more other LEDs in the planar array to receive or convey the lighting instructions.

4. The system of claim 3, wherein the light assembly further comprise a second planar array of LEDs serially connected to the planar array of LEDs, wherein a single serial connection controls the LEDs of the first and second planar arrays.

5. The system of claim 3, wherein the LEDs use a frequency of 20,000 Hz or more.

6. The system of claim 1, wherein the light assembly comprises a partial cube-configuration comprising the planar surface and side surfaces attached to and extending orthogonally from the planar surface, wherein the planar surface and the side surfaces comprise planar arrays of serially connected light emitting diodes (LEDs).

7. The system of claim 6, wherein dimensions of the planar surface and the side surfaces are configured based on dimensions of the planar arrays of LEDs and the camera.

8. The system of claim 6, wherein each of the planar arrays of LEDs comprises an 8×8 array of LEDs or a 16×16 array of LEDs.

9. The system of claim 1, wherein the image capture device further comprises a frame attaching to the motor to support the motor, the light assembly, and the camera above the object, the frame comprising legs that extend outward away from the object and downward to a floor surface.

10. The system of claim 1, wherein the camera comprises:

an electronic sensor or photographic film onto which the images of the object are recorded; and a wide angle lens having an angle of view of 64 degrees or more.

11. The system of claim 1, wherein the motor is configured to translate the light assembly and camera on three axes of movement.

12. The system of claim 1, wherein the motor is configured to translate the light assembly and camera on two axes of movement laterally above the object and on an up and down axis.

13. A system for determining reflectance properties of an object using images of the object, the system comprising:

an image capture means for capturing images of the object under variable image capture conditions using a planar array of lights;

a control means for instructing the image capture means to position the lights and camera using a motor, illuminate lights, and capture the images the images of the object under the variable image capture conditions using the camera;

and a reflectance property determining means for determining the reflectance properties of the object using the images of the object captured by the image capture means, wherein the determining the reflectance property includes determining a bi-directional reflectance distribution function (BRDF) based on the images, the BDRF providing pixel colors of a representation of the object for different light directions and camera directions.

14. The system of claim 13, wherein the image capture means comprises:

a light assembly comprising the planar array of lights attached on a side of a planar surface of the light assembly, the lights individually addressable and configured to illuminate based on receiving lighting instructions;

a camera attached to the light assembly in a position relative to the lights to receive light from the object illuminated by the lights to capture images of the object, the camera configured to capture images of the object based on receiving camera instructions;

and the motor attached to the light assembly and configured to move the lights and camera relative to the object based on receiving motor instructions.

15. The system of claim 13, wherein the reflectance property determining means comprises instructions stored on a non-transitory computer readable medium that, when executed by a processor, perform operations comprising:

receiving the images from the image capture means.

16. The system of claim 15, wherein determining the BRDF based on the images further comprises:

identifying a respective light used to light the each of the images;

determining adjustments based on calibration information for the images; and determining the BDRF based on the images and the adjustments of the images.

17. The system of claim 16, wherein the calibration information is determined by capturing calibration images of a single color surface and determining a brightness of individual lights at different locations on the surface.

18. A method for capturing images of an object for use in determining reflectance properties of the object, the method comprising:

identifying camera directions and light directions to be used in capturing images for use in determining reflectance properties of the object, wherein the camera directions and light directions are identified to provide a number of different views of the object from different camera directions and with the object illuminated from different light directions, the number and diversity of the different views sufficient to determine the reflectance properties of the object with a specified resolution;

identifying image capture conditions for capturing the images of the object, the image capture conditions specifying different camera positions to capture the images of the object from the different camera directions, the image capture conditions further specifying illuminating lights to capture the images with the object illuminated from the different lighting directions; and controlling an image capture device to capture the images under the image capture conditions, wherein controlling the image capture device comprises providing instructions to the image capture device to position a planar array of lights and camera using the motor, illuminate lights of the planar array of lights, and capture the images under the image capture conditions using the camera.

19. The method of claim 18, wherein identifying the image capture conditions comprises, for individual images:

determining a respective position of the camera and planar array of lights relative to the object and a respective selection of the lights to illuminate to capture the respective image from a respective camera direction and with the object illuminated from a respective light direction.

20. The method of claim 19, wherein controlling the image capture device to capture the images comprises, for individual images:

providing a motor instruction causing the motor to move the camera and planar array of lights into the respective position;

providing a lighting instruction to illuminate the respective selection of lights; and providing a camera instruction to capture the respective image.

* * * * *